(12) United States Patent
Park et al.

(10) Patent No.: US 11,571,350 B2
(45) Date of Patent: Feb. 7, 2023

(54) MEDICAL DIAGNOSIS DEVICE AND MEDICAL DIAGNOSIS METHOD USING SAME

(71) Applicant: SAMSUNG MEDISON CO., LTD., Gangwon-do (KR)

(72) Inventors: Dai-un Park, Gangwon-do (KR); Kyeong-gu Woo, Gangwon-do (KR); Jun-pil Moon, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 850 days.

(21) Appl. No.: 16/335,938

(22) PCT Filed: Sep. 15, 2017

(86) PCT No.: PCT/KR2017/010147
§ 371 (c)(1),
(2) Date: Mar. 22, 2019

(87) PCT Pub. No.: WO2018/056651
PCT Pub. Date: Mar. 29, 2018

(65) Prior Publication Data
US 2019/0307628 A1    Oct. 10, 2019

Related U.S. Application Data

(63) Continuation of application No. 15/702,167, filed on Sep. 12, 2017, now Pat. No. 11,103,408.
(Continued)

(51) Int. Cl.
*A61G 15/00*    (2006.01)
*A61B 5/01*    (2006.01)
(Continued)

(52) U.S. Cl.
CPC .............. *A61G 15/005* (2013.01); *A61B 5/01* (2013.01); *A61B 5/1072* (2013.01);
(Continued)

(58) Field of Classification Search
CPC ................................ A61G 15/005; A61B 5/01
See application file for complete search history.

(56) References Cited

U.S. PATENT DOCUMENTS 6,063,035 A    5/2000   Sakamoto et al.
6,629,927 B1   10/2003  Mesaros et al.
(Continued)

FOREIGN PATENT DOCUMENTS

CN    201572283 U    9/2010
CN    102076262 A    5/2011
(Continued)

OTHER PUBLICATIONS

Chinese Office Action dated Jun. 23, 2021 issued in Chinese Patent Application No. 201780072356.8.
(Continued)

*Primary Examiner* — Joseph M Santos Rodriguez
(74) *Attorney, Agent, or Firm* — Morgan, Lewis & Bockius LLP

(57) ABSTRACT

Provided are a medical diagnosis apparatus and a medical diagnosis method using the same. According to an embodiment, the medical diagnosis apparatus may include: a main body; a chair unit movably supported by the main body and on which an object is positioned; a diagnosis part that is movably connected to the main body and is spaced apart from the chair unit by a preset first distance in one plane; a controller configured to generate a control signal for moving the diagnosis part according to preset information; and a first driving device configured to generate a driving force for moving the diagnosis part according to the control signal.

13 Claims, 22 Drawing Sheets

Related U.S. Application Data

(60) Provisional application No. 62/398,689, filed on Sep. 23, 2016.

(51) Int. Cl.

| | | |
|---|---|---|
| *A61B 5/00* | (2006.01) | |
| *A61B 8/00* | (2006.01) | |
| *A61G 15/02* | (2006.01) | |
| *A61G 15/12* | (2006.01) | |
| *A61B 5/1171* | (2016.01) | |
| *A61B 5/1172* | (2016.01) | |
| *A61B 5/107* | (2006.01) | |
| *A61B 8/08* | (2006.01) | |
| *A61B 8/14* | (2006.01) | |
| *A61G 5/12* | (2006.01) | |
| *A61B 50/10* | (2016.01) | |
| *A61B 5/103* | (2006.01) | |

(52) U.S. Cl.
CPC .......... *A61B 5/1172* (2013.01); *A61B 5/1176* (2013.01); *A61B 5/4306* (2013.01); *A61B 5/4362* (2013.01); *A61B 5/70* (2013.01); *A61B 8/08* (2013.01); *A61B 8/14* (2013.01); *A61B 8/40* (2013.01); *A61B 8/4209* (2013.01); *A61B 8/4218* (2013.01); *A61B 8/4433* (2013.01); *A61B 8/461* (2013.01); *A61B 8/585* (2013.01); *A61G 15/02* (2013.01); *A61G 15/12* (2013.01); *A61B 5/103* (2013.01); *A61B 8/0866* (2013.01); *A61B 50/10* (2016.02); *A61B 2503/02* (2013.01); *A61G 5/128* (2016.11); *A61G 2203/30* (2013.01)

(56) References Cited

U.S. PATENT DOCUMENTS

| | | | |
|---|---|---|---|
| 6,663,569 B1 | 12/2003 | Wilkins et al. | |
| 6,716,167 B1 * | 4/2004 | Henderson | A61B 8/4405 |
| | | | 600/437 |
| 6,958,577 B2 | 10/2005 | Biglieri et al. | |
| 8,376,103 B1 | 2/2013 | Sliger | |
| 8,449,455 B2 | 5/2013 | Honda et al. | |
| 9,204,860 B2 | 12/2015 | Ji et al. | |
| 9,235,973 B2 | 1/2016 | Popescu | |
| 9,492,341 B2 | 11/2016 | Huster et al. | |
| 9,610,197 B2 | 4/2017 | Wellhofer | |
| 2007/0252068 A1 | 11/2007 | Secora | |
| 2008/0300489 A1 | 12/2008 | Schutz et al. | |
| 2011/0071414 A1 * | 3/2011 | Heil | A61B 5/746 |
| | | | 600/511 |
| 2011/0104634 A1 | 5/2011 | Kyostila | |
| 2012/0089419 A1 | 4/2012 | Huster et al. | |
| 2013/0072787 A1 * | 3/2013 | Wallace | A61B 90/50 |
| | | | 600/424 |
| 2013/0165796 A1 | 6/2013 | Tashiro | |
| 2014/0107487 A1 | 4/2014 | Kim et al. | |
| 2015/0366534 A1 | 12/2015 | Nair et al. | |
| 2016/0202093 A1 | 7/2016 | Stanton et al. | |
| 2016/0270764 A1 | 9/2016 | Wodecki | |

FOREIGN PATENT DOCUMENTS

| | | |
|---|---|---|
| CN | 103096808 A | 5/2013 |
| EP | 1292259 B1 | 8/2013 |
| JP | H08-000684 A | 1/1996 |
| JP | 2009291281 A | 12/2009 |
| JP | 2011-036589 A | 2/2011 |
| JP | 2011-072418 A | 4/2011 |
| JP | 2011-182978 A | 9/2011 |
| JP | 2012-095934 A | 5/2012 |
| JP | 2014-004364 A | 1/2014 |
| JP | 2015-128474 A | 7/2015 |
| JP | 2018-171385 A | 11/2018 |
| KR | 10-2005-119921 A | 12/2005 |
| KR | 10-0968309 B1 | 7/2010 |
| KR | 10-1036788 B1 | 5/2011 |
| KR | 10-1268793 B1 | 5/2013 |
| KR | 10-2014-0046754 A | 4/2014 |
| KR | 10-2015-0019147 A | 2/2015 |
| KR | 10-2015-0052673 A | 5/2015 |
| KR | 10-1652538 B1 | 8/2016 |
| KR | 10-1660833 B1 | 9/2016 |
| WO | 2005/120331 A1 | 12/2005 |
| WO | 2010/150697 A1 | 12/2010 |
| WO | 2013/112107 A1 | 8/2013 |

OTHER PUBLICATIONS

Extended European Search Report dated May 4, 2020 issued in European Patent Application No. 17853339.4.
Written Opinion and International Search Report dated Dec. 22, 2017 issued in International Patent Application Mo. PCT/KR2017/010147 (with English translation).
Written Opinion and International Search Report dated Dec. 20, 2017 issued in International Patent Application No. PCT/KR2017/009966 (with English translation).
Extended European Search Report dated Jun. 4, 2019 issued in European Patent Application No. 17853365.9.
Chinese Office Action dated Feb. 15, 2022 issued in Chinese Patent Application No. 201780072356.8 (with English translation).
European Office Action dated Apr. 12, 2022 issued in European Patent Application No. 17853365.9.
Korean Notice of Allowance dated Sep. 14, 2022 issued in Korean Patent Application No. 10-2017-0118854 (with English translation).
Korean Office Action dated Jul. 8, 2022 issued in Korean Patent Application No. 10-2017-0118854 (with English translation).
Chinese Office Acton dated Jul. 5, 2022 issued in Chinese Patent Application No. 201780072356.8 (with English translation).

* cited by examiner

MEDICAL DIAGNOSIS DEVICE AND MEDICAL DIAGNOSIS METHOD USING SAME

CROSS REFERENCE

This application is the U.S. National Phase under 35 U.S.C. § 371 of International Application No. PCT/KR2017/010147 filed on Sep. 15, 2017, which claims the benefit of U.S. patent application Ser. No. 15/702,167 filed on Sep. 12, 2017 and U.S. Provisional Application No. 62/398,689 filed on Sep. 23, 2016, the entire contents of each are hereby incorporated by reference.

TECHNICAL FIELD

The present disclosure relates to a medical diagnosis apparatus including an ultrasound probe for providing an ultrasound image and a medical chair unit and a medical diagnosis method.

BACKGROUND ART

Ultrasound diagnosis apparatuses transmit an ultrasound signal generated by a transducer of a probe to an object and receive information about a signal reflected from the object, thereby obtaining an image of an internal part of the object (e.g., soft tissue or blood flow) in a non-invasive manner.

Because ultrasound diagnosis apparatuses are compact, affordable, display images in real-time, and are highly safe for a fetus due to lack of radiation exposure compared to other types of imaging diagnosis apparatuses such as an X-ray diagnostic apparatus, a computerized tomography (CT) scanner, a magnetic resonance imaging (MRI) apparatus, a nuclear medicine diagnostic apparatus, etc., such ultrasound diagnosis apparatuses have been widely used for medical diagnosis.

An ultrasound diagnosis apparatus includes a medical chair unit on which a probe and an object can be positioned. In obstetrical and gynecological diagnosis during which ultrasound probes are widely used, an external condition of a pregnant woman corresponding to an object rapidly changes, and according to a change in a diagnostic posture of the pregnant woman due to changes in an external appearance of the pregnant woman and diagnostic items, relative positions of a medical chair on which the pregnant woman is seated for obstetrical or gynecological examination, a probe holder for holding probes, and a diagnosis part also need to be changed.

DESCRIPTION OF EMBODIMENTS

Technical Problem

Provided is a medical diagnosis apparatus including an accessory unit of which a position and a form automatically or manually change according to body information of an object and medical information of the object.

Provided is also a medical diagnosis apparatus including an accessory unit of which a position is automatically controlled such that interference with an object may not occur according to a diagnostic mode for the object.

Solution to Problem

According to an aspect of the present disclosure, a medical diagnosis apparatus may include: a main body; a chair unit movably supported by the main body and on which an object is positioned; a diagnosis part that is movably connected to the main body and is spaced apart from the chair unit by a preset first distance in one plane; a controller configured to generate a control signal for moving the diagnosis part according to preset information; and a first driving device configured to generate a driving force for moving the diagnosis part according to the control signal.

The chair unit and the diagnosis part may be spaced apart from each other by a preset first height along a direction perpendicular to the one plane.

The medical diagnosis apparatus may further include: a first sensor configured to detect a position of the diagnosis part, which varies depending on the driving force generated by the first driving device; and a first limit switch configured to stop the first driving device as the diagnosis part and the chair unit are arranged adjacent to each other with a distance or height therebetween that is less than or equal to the preset first distance or the preset first height.

The first distance that is a distance between a center line in a longitudinal direction of the chair unit and a center line of the diagnosis part extending in a direction parallel to the center line may be in a range of 40 cm to 90 cm.

The chair unit may include an upper body support, a seat, and a leg rest sequentially arranged in one direction and connected to one another, and the first height between the seat and a lower end of the diagnosis part may be in a range of 5 cm to 70 cm.

The medical diagnosis apparatus may further include a storage storing first body information of the object and an input interface configured to input identification information of the object, the first body information of the object may be identified by the identification information of the object, and the identification information of the object may be at least one of name information of the object, fingerprint information of the object, face information of the object, and an identification code corresponding to the object.

When the medical diagnosis apparatus is an obstetrical and gynecological diagnosis apparatus, the first body information of the object may be at least one of a gestational age, the number of fetuses, a fetal position, a weight, a height, a body temperature, an examination history, and a medical history.

The medical diagnosis apparatus may further include a first connector that connects the diagnosis part to the main body and is configured such that the diagnosis part is movable with respect to the main body, and the first connector may include: a first engaging member rotatably coupled to the main body; a first arm that extends in one direction and is hinged with the first engaging member; a second engaging member rotatably coupled to the first arm; a second arm that extends in one direction and is hinged with the second engaging member; and a connection member having one end coupled to the diagnosis part and the other end hinged to the second arm.

The first driving device may be a traction motor, and the first sensor may include an encoder configured to detect a driving state of the traction motor.

The medical diagnosis apparatus may further include: an ultrasound diagnosis device including at least one ultrasound probe and a probe holder that is movably connected to the main body; and a second driving device configured to generate a driving force for moving the ultrasound diagnosis device, and the ultrasound diagnosis device may be spaced apart from the chair unit by a preset second distance in one plane, and the controller may generate a control signal for moving the ultrasound diagnosis device according to preset information.

The chair unit and the ultrasound diagnosis device may be spaced apart from each other by a preset second height along a direction perpendicular to the one plane.

The medical diagnosis apparatus may further include: a second sensor configured to detect a position of the ultrasound diagnosis device, which varies depending on the driving force generated by the second driving device; and a second limit switch configured to stop the second driving device as the diagnosis part and the chair unit are arranged adjacent to each other with a distance or a height therebetween that is less than or equal to the preset second distance or the preset second height.

The second distance that is a distance between the center line in the longitudinal direction of the chair unit and a center line of the probe holder extending in a direction parallel to the center line may be in a range of 35 cm to 85 cm.

The chair unit may include an upper body support, a seat, and a leg rest sequentially arranged in one direction and connected to one another, and the second height between the seat and a lower end of the probe holder may be in a range of 5 cm to 70 cm.

The medical diagnosis apparatus may further include a probe sensor configured to detect a state in which the at least one ultrasound probe has been held on the probe holder.

According to another aspect of the present disclosure, a medical diagnosis method may include: acquiring first body information of an object; generating a control signal for a chair unit, an ultrasound diagnosis device, and a diagnosis part based on the first body information of the object; changing, according to the control signal, the chair unit, the ultrasound diagnosis device, and the diagnosis part from an initial state to a diagnostic state; receiving diagnosis completion information; and changing the chair unit, the ultrasound diagnosis device, and the diagnosis part from the diagnostic state to the initial state.

The medical diagnosis method may further include: detecting positions of the ultrasound diagnosis device and the diagnosis part that vary depending on driving forces generated by first and second driving devices; and stopping driving by the first and second driving devices when a distance or height between the chair unit and either the ultrasound diagnosis device or the diagnosis part is in a range that is less than or equal to a predetermined range.

The medical diagnosis method may further include inputting identification information of the object, the first body information of the object may be acquired based on the identification information of the object, and the identification information of the object may be at least one of name information of the object, fingerprint information of the object, face information of the object, and an identification code corresponding to the object.

When the medical diagnosis method is an obstetrical and gynecological diagnosis method, the first body information of the object may be at least one of a gestational age, the number of fetuses, a weight, a height, a body temperature, a medical history, and a fetal position.

When at least one ultrasound probe included in the ultrasound diagnosis device, is held on a probe holder for a certain period of time, the diagnosis completion information may be input.

Advantageous Effects of Disclosure

According to an embodiment, a medical diagnosis apparatus allows a form of an accessory unit to automatically change according to body information and medical information of an object, thereby increasing user convenience and minimizing diagnosis time.

Furthermore, according to an embodiment, a medical diagnosis apparatus allows a position of an accessory unit to be automatically controlled such that interference with an object may not occur according to a diagnostic mode for the object, thereby improving safety of the object and user convenience and preventing damage to the medical diagnosis apparatus.

BRIEF DESCRIPTION OF DRAWINGS

These and/or other aspects will become more readily appreciated from the following description of the embodiments, taken in conjunction with the accompanying drawings, in which reference numerals denote structural elements.

MODE OF DISCLOSURE

Figure 1:
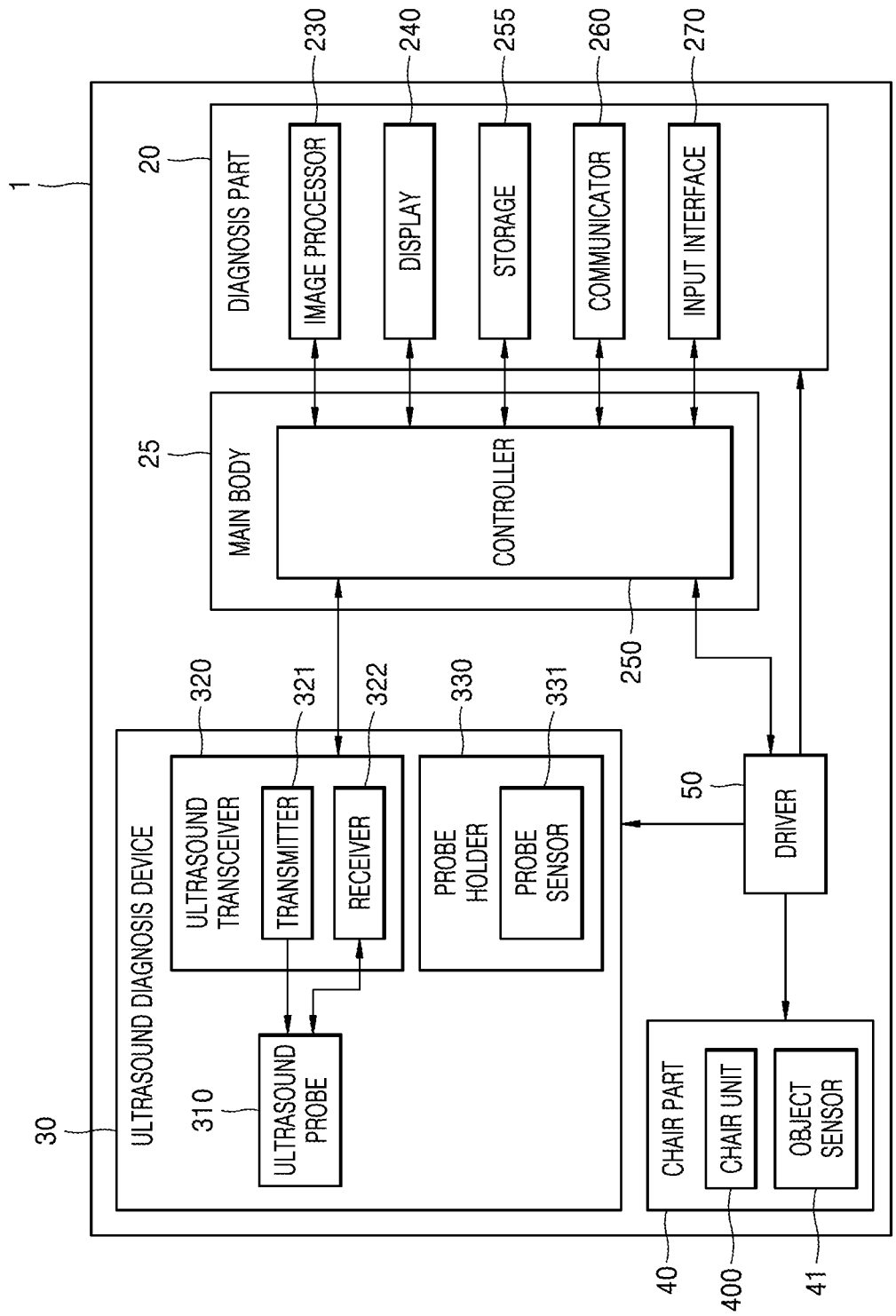
FIG. 1 is a block diagram of a configuration of a medical diagnosis apparatus according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Hereinafter, the operating principles and embodiments of the present disclosure will be described in detail with reference to the accompanying drawings.

Furthermore, in the present specification, an "object" may be a target to be imaged and include a patient, a pregnant woman, a fetus, or a part thereof. For example, the object may include a part of an organ in a pregnant woman's body, a fetus, or a phantom.

Throughout the specification, a "user" may be, but is not limited to, a medical expert, e.g., a medical doctor, a nurse, a medical laboratory technologist, a medical imaging expert, etc.

Throughout the specification, an "ultrasound image" refers to an image of an object, which is formed by processing ultrasound signals transmitted to and reflected from the object.

Embodiments will be described more fully hereinafter with reference to the accompanying drawings.

Figure 2:
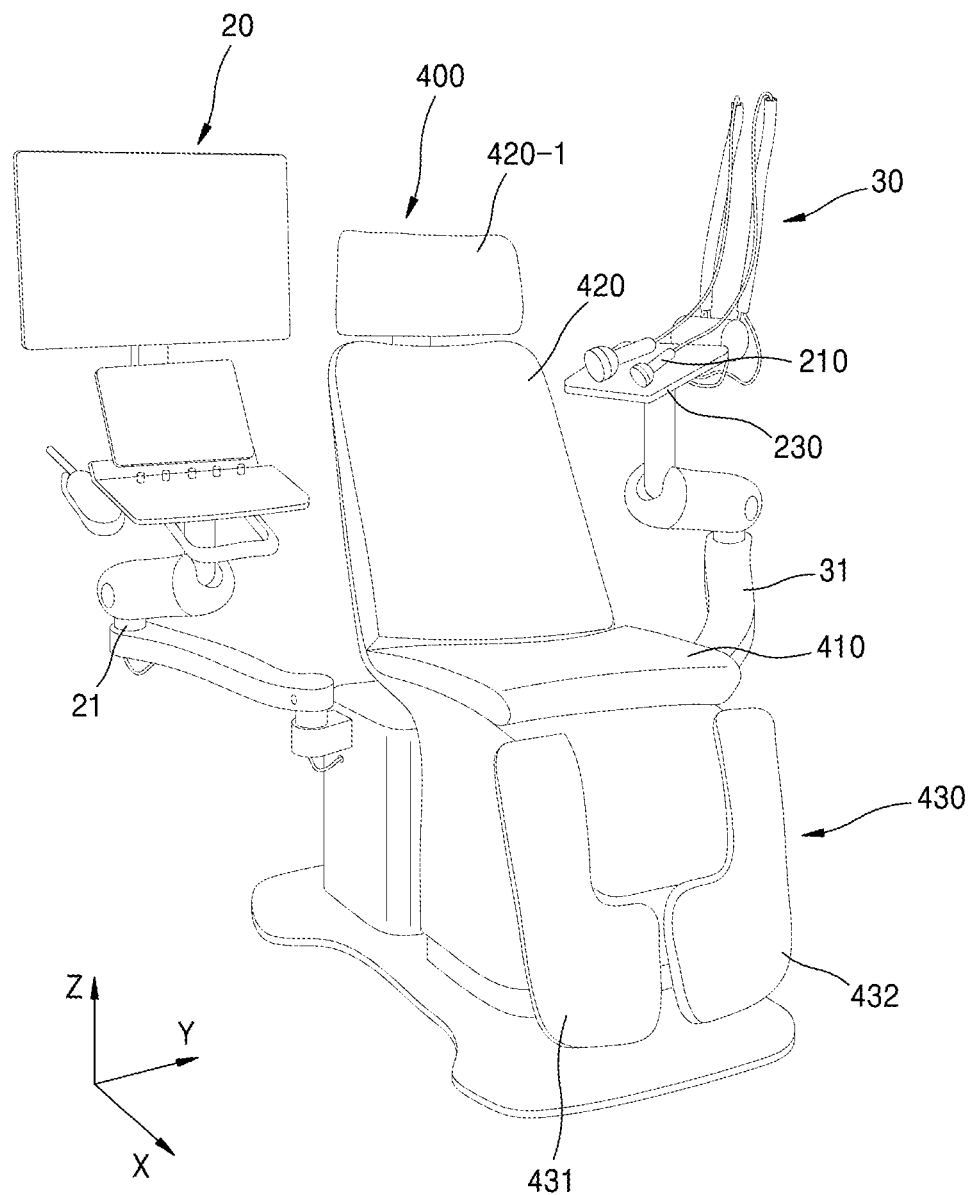
FIG. 2 is a perspective view of a medical diagnosis apparatus according to an embodiment.

FIG. 1 is a block diagram of a configuration of a medical diagnosis apparatus 1 according to an embodiment. FIG. 2 is a perspective view of a medical diagnosis apparatus according to an embodiment.

Referring to FIGS. 1 and 2, the medical diagnosis apparatus 1 according to the embodiment may include an ultrasound diagnosis device 30, a main body 25, a diagnosis part 20 that may be used by a user to manipulate the medical diagnosis apparatus 1 for diagnosing an object, and a chair part 40 in which the object may be positioned. Hereinafter, while an obstetrical and gynecological diagnosis apparatus has been described as an example of the medical diagnosis apparatus 1, embodiments of the present disclosure are not limited thereto, and the technical idea of the present specification may be applied to another medical diagnosis apparatus 1 including the diagnosis part 20, the ultrasound diagnosis device 30, and the chair part 40 that are arranged to be separated from one another.

According to an embodiment, the diagnosis part 20 may include an image processor 230 for processing a received signal into an image, a display 240 for outputting the image, a storage 255, a communicator 260, and an input interface 270.

The image processor 230 generates an ultrasound image by using ultrasound data generated by an ultrasound receiver 322.

The display 240 may display a generated ultrasound image and various pieces of information processed by the medical diagnosis apparatus 1. The display 240 may include one or a plurality of displays, e.g., a first display for a user and a second display for an object, according to its implemented configuration. In this case, the display may be combined with a touch panel to form a touch screen.

The storage 255 may store various data or programs for driving and controlling the medical diagnosis apparatus 1, input and/or output ultrasound data, obtained ultrasound images, identification (ID) information and body information of an object, ID information and body information of a user, etc.

In the present specification, ID information of an object or user means at least one of all types of information used to identify the object or individual user, such as a name, a resident registration number, a birth date, a personal ID number, a personal ID code, and biometric recognition information such as a face, an iris, a fingerprint, etc. Furthermore, in the present specification, body information of an object means all pieces of body information of the object for medical treatment, such as a pregnant woman's gestational age, the number of fetuses, a fetal position, a pregnant woman's weight, stature, body temperature, examination history, medical history, etc. Furthermore, in the present specification, a user's body information means all pieces of user's body information needed during diagnosis, such as an operator's operating posture, stature (a height and a sitting height), arm length, gaze position, etc.

According to an embodiment, the medical diagnosis apparatus 1 may include the communicator 260 and may be connected to external apparatuses (e.g., central servers, medical apparatuses, portable devices such as smartphones, tablet PCs, wearable devices, etc.) via the communicator 260.

The communicator 260 may include at least one element capable of communicating with the external apparatuses, for example, at least one of a local area communication module, a wired communication module, and a wireless communication module.

For example, the communicator 260 may transmit ID information of an object and a user to an external apparatus such as a central server, and the external apparatus may transmit data related to body information of the object and the user, corresponding to the received ID information of the object and the user, to the controller 250 so that the controller 250 may control the medical diagnosis apparatus 1 according to the received data related to body information of the object and the user. The external apparatus may include a recording medium having recorded thereon the data related to body information of the object and the user.

The input interface 270 may receive a user input for controlling the medical diagnosis apparatus 1. For example, the user may input to the input interface 270 ID information of the object, ID information of the user, or a manipulation signal for adjusting a position of the chair part 40 that will be described below. In this case, the user input may include, but is not limited to, an input of manipulating a button, a key pad, a mouse, a trackball, a jog switch, a knob, etc., an input of touching a touch pad or touch screen, a voice input, a motion input, an input of biometric information, etc.

According to an embodiment, the main body 25 may include the controller 250 for controlling the medical diagnosis apparatus 1 and support the diagnosis part 20, the ultrasound diagnosis device 30, and the chair part 40.

The controller 250 may control all operations of the medical diagnosis apparatus 1 and flow of signals between the internal components of the medical diagnosis apparatus 1. The controller 250 may include a memory storing data or programs for performing functions of the medical diagnosis apparatus 1 and a processor processing the programs or data. Furthermore, the controller 250 may control an operation of the medical diagnosis apparatus 1 by receiving a control signal from the input interface 270 or an external apparatus.

According to an embodiment, the ultrasound diagnosis device 30 may include an ultrasound probe 310 and an ultrasound transceiver 320 for transmitting or receiving ultrasound waves. The ultrasound probe 310 may include a plurality of transducers. The plurality of transducers may transmit ultrasound signals to an object in response to transmitting signals applied by a transmitter 321 included in the ultrasound transceiver 320. The plurality of transducers may receive ultrasound signals reflected from the object to generate reception signals. In this case, the ultrasound probe 310 may be formed integrally with the medical diagnosis apparatus 1, or may be separate from the medical diagnosis apparatus 1 but be connected thereto by wire or wirelessly. In addition, the medical diagnosis apparatus 1 may include one or a plurality of ultrasound probes 310 according to its implemented configuration.

According to an embodiment, the ultrasound diagnosis device 30 may further include a probe holder 330 for holding the ultrasound probe 310 in addition to the ultrasound probe 310 and the ultrasound transceiver 320. The user may use the ultrasound probe 310 to diagnose an object and place the ultrasound probe 310 on the probe holder 330 after diagnosis is stopped or completed.

The probe holder 330 may further include a probe detector 331 for detecting whether the ultrasound probe 310 has been held on the probe holder 330. The probe detector 331 may be located on at least one inner wall of the probe detector 330, but is not limited thereto. For example, the probe detector 331 may be a weight sensor for sensing a weight of the ultrasound probe 310, a micro switch or piezoelectric sensor pressed by the ultrasound probe 310, an optical sensor, or the like. For example, when the probe detector 331 detects that the ultrasound probe 310 has been held on the probe holder 330 for a certain period of time, e.g., for sixty (60) seconds or more, it may be recognized that diagnosis with regard to the object is completed.

According to an embodiment, the chair part 40 may include a chair unit 400 in which the object may be positioned and one or more object sensors 41 capable of acquiring body information of the object. The chair unit 400 is sufficiently long so that the object may be positioned therein. A length direction of the chair unit 400 is parallel to a length direction or height direction of the object. The chair unit 400 may be supported to be fixed to the floor or be movable. For example, the chair unit 400 may move vertically to allow the object to ascend or descend or may be inclined to adjust a diagnosis angle with respect to the object.

According to an embodiment, the chair unit 400 may include a seat 410 and an upper body support 420 with a slope adjustable with respect to the seat 410. The seat 410 may support a lower body of the object while the upper body support 420 supports an upper body of the object. The upper body support 420 may include a head support 420-1 for supporting a head of the object. The head support 420-1 may be detachably fixed to the upper body support 420, and may be detached from the upper body support 420 according to a diagnostic state. The chair unit 400 may further include a leg rest 430 on which legs of the object rest. According to an embodiment, the leg rest 430 may include a first rest 431 and a second rest 432 capable of respectively supporting the right and left legs. However, the chair unit 400 is not limited thereto, and may also be applied to a support capable of supporting an object, such as a chair having a different shape or a bed.

According to an embodiment, the user may adjust, according to a diagnostic state of the object, an angle of the upper body support 420 with respect to the seat 410 or an angle of the leg rest 430 with respect to the seat 410. Furthermore, the first and second rests 431 and 432 included in the leg rest 430 may be adjusted at various angles to be separated from each other according to a diagnostic state of the object.

The object sensor 41 is a sensing device capable of detecting a state of the object positioned on the chair unit 400. For example, the object sensor 41 may include a weight sensor capable of measuring in real-time measurement information of the object, such as a weight of the object, a temperature sensor capable of detecting a change in a temperature of the object, a time sensor capable of detecting and calculating a sitting duration of time, or an operation sensor capable of detecting a sudden change in a sitting state of the object. Accordingly, the object sensor 41 may detect measurement information of the object and a sudden change in a sitting state of the object, which occurs during a diagnostic process, and transmit the measurement information of the object, position movement information of the object, etc. to the controller 250.

Referring back to FIG. 1, according to an embodiment, a driver 50 may generate a driving force capable of moving and changing the shapes of the diagnosis part 20, the ultrasound diagnosis device 30, and the chair part 40 according to a control signal from the controller 250. When the object is a pregnant woman carrying a fetus, her external appearance rapidly changes according to the growth of the fetus, and diagnostic items also change according to the growth of the fetus. When a diagnostic posture of the pregnant woman changes due to the changes in the external appearance of the pregnant woman and diagnostic items, a shape of the chair part 40 in which the pregnant woman is positioned to receive an obstetric or gynecological diagnosis has to be changed, and positions of the diagnosis part 20 and the ultrasound diagnosis device 30 need to be changed to provide the user with usage convenience. Generation of a control signal for controlling the driver 50 according to the body information of the object and the body information of the user and automatic movement of the diagnosis part 20, the ultrasound diagnosis device 30, and the chair part 40 according to a diagnostic state of the object based on the control signal will be described in more detail below.

Figure 3:
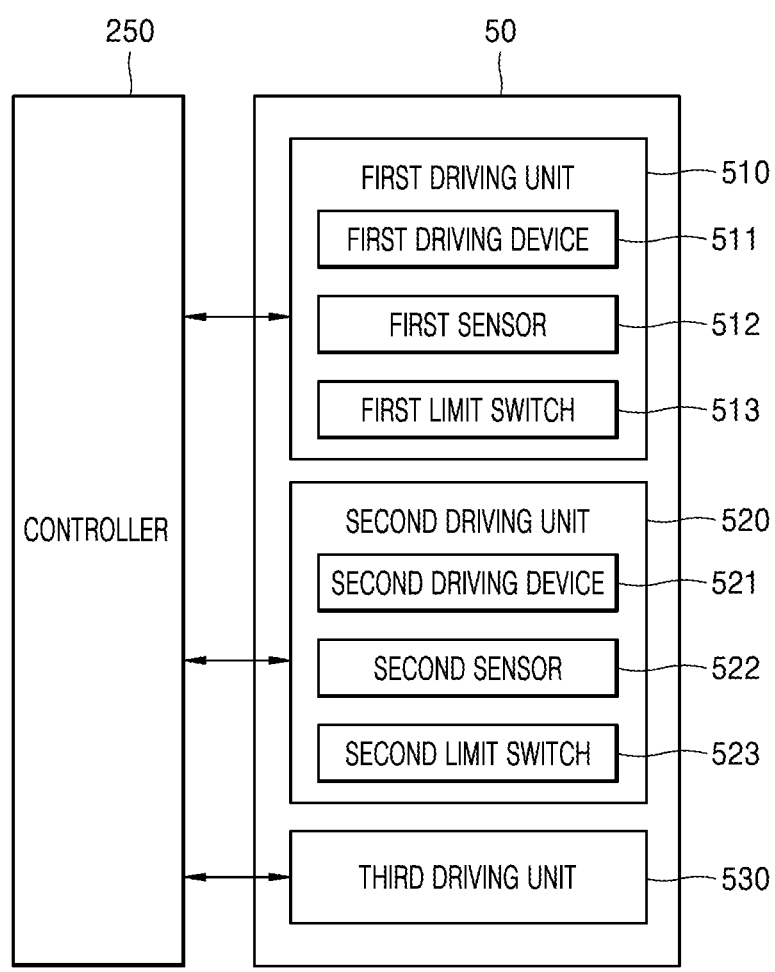
FIG. 3 is a block diagram of a configuration of a driver and a controller according to an embodiment.
Figure 4A:
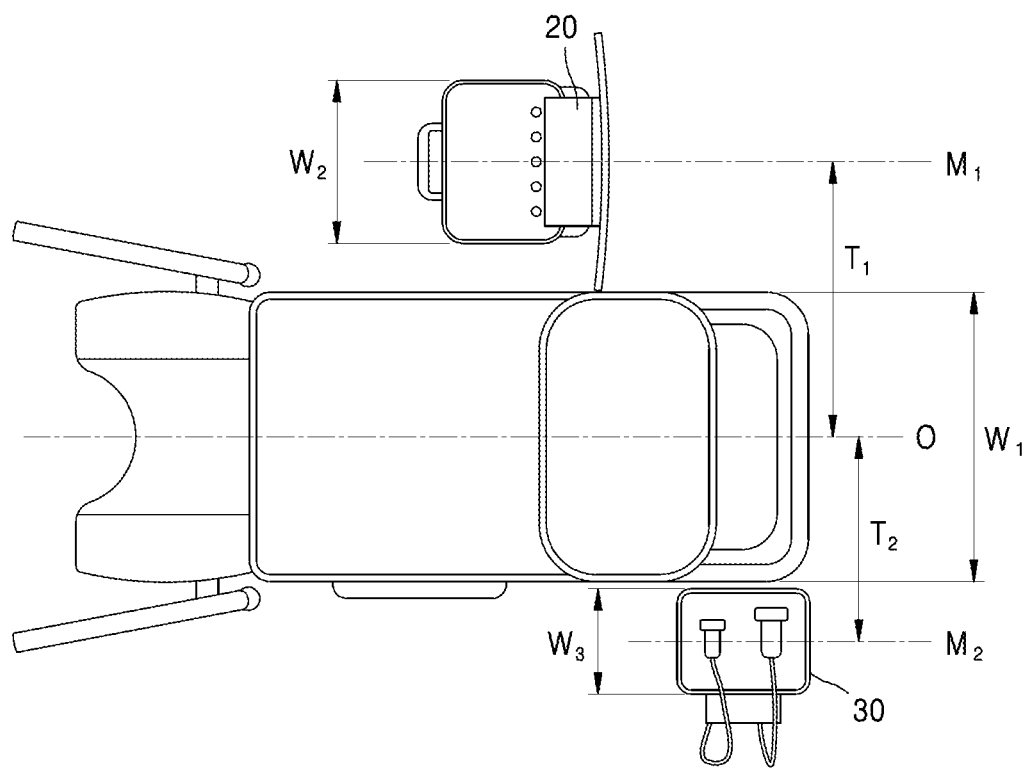
FIG. 4A is a plan view of a medical diagnosis apparatus according to an embodiment.
Figure 4B:
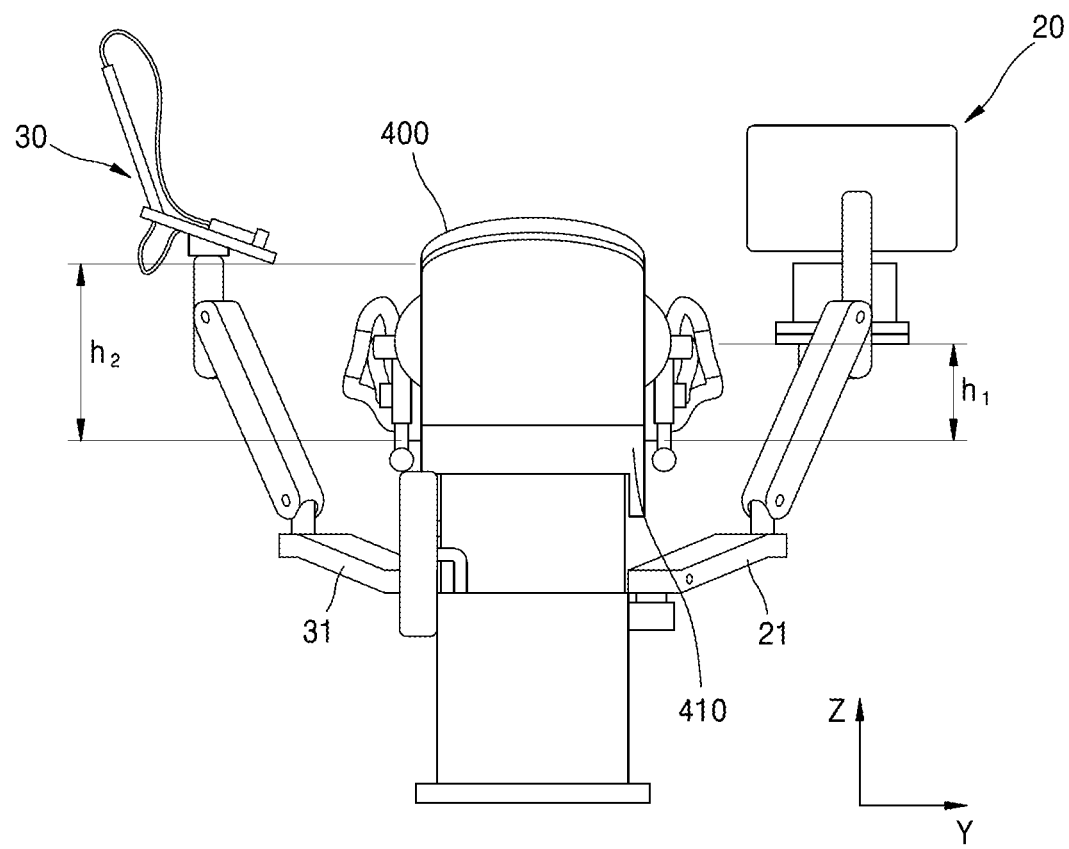
FIG. 4B is a side view of a medical diagnosis apparatus according to an embodiment.

FIG. 3 is a block diagram of a configuration of a driver and a controller according to an embodiment. FIG. 4A is a plan view of a medical diagnosis apparatus according to an embodiment. FIG. 4B is a side view of a medical diagnosis apparatus according to an embodiment.

According to an embodiment, the user may perform diagnosis using the medical diagnosis apparatus 1 by being located adjacent to the upper or lower body of the object according to preset information such as body information of the object, a diagnostic state of the object, a user input, and preset state information. Thus, to improve usage convenience of the user, positions of the diagnosis part 20 and the ultrasound diagnosis device 30 used by the user need to be changed according to preset information.

According to an embodiment, when the object, the diagnosis part 20, and the ultrasound diagnosis device 30 are arranged within a predetermined range such that they interfere with one another, this arrangement may cause damage to the object. Thus, when the diagnosis part 20 and the ultrasound diagnosis device 30 are arranged within a predetermined range from the object, it is needed to physically or controllably stop movement of the diagnosis part 20 and the ultrasound diagnosis device 30. An embodiment to be described below presents the technical idea in which when the diagnosis part 20 and the ultrasound diagnosis device 30 are arranged adjacent to the object positioned on the chair unit 400, operations of a first driving device 511 and a second driving device 521 configured to generate driving forces for respectively driving the diagnosis part 20 and the ultrasound diagnosis device 30 may be stopped controllably or physically by using first and second limit switches 513 and 514.

Referring to FIGS. 2 and 3, according to an embodiment, the driver 50 may include a first driving unit 510 for moving the diagnosis part 20, a second driving unit 520 for moving the ultrasound diagnosis device 30, and a third driving unit 530 for moving the chair part 40.

According to an embodiment, the first driving unit 510 may include the first driving device 511 that is positioned between the diagnosis part 20 and the main body 25 to transmit a driving force to a first connector 21 connecting between the diagnosis part 20 and the main body 25, a first sensor 512 capable of detecting a position of the diagnosis part 20 by sensing a driving state of the first driving device 511, and the first limit switch 513 capable of stopping driving by the first driving device 511 in a critical condition.

The first driving device 511 is a driving motor capable of generating a driving force that is transmitted to the first connector 21. For example, the first driving device 511 may be a traction motor including a stator and a rotor located at a central part of the stator. When the first driving device 511 is a traction motor, it is possible to continuously check a driving force that is provided to the first connector 21 by detecting a position of a magnet included in a rotor and the number of rotations of a rotor core in the rotor via the first sensor 512 as described below. However, in the present specification, the first driving device 511 is not limited to a traction motor and may be any driving device capable of transmitting a driving force to the first connector 21 while continuously checking the driving force that is transmitted to the first connector 21.

The first sensor 512 is a position sensor capable of detecting a position of the diagnosis part 20, which varies depending on a driving force generated by the first driving device 511. For example, the first sensor 512 may include an optical encoder consisting of a light source such as light emitting diode (LED) and a light-receiver such as a photo diode, a photo transistor or a photo resistor, or may include a magnetic encoder consisting of a permanent magnet and a magnetic field sensor such as a hall sensor or magneto resistive (MR) sensor. When the first sensor 512 includes an encoder, the first sensor 512 may detect a change in the position of the diagnosis part 20 due to the first driving device 511 by sensing a driving state of the first driving device 511, which is transmitted to the first connector 21, and transmitting the driving state to the controller 250. However, in the specification, the first sensor 512 is not limited to an optical or magnetic encoder, and may be any sensor capable of continuously identifying the position of the diagnosis part 20 that varies depending on a driving force generated by the first driving device 511.

The first limit switch 513 is a control device capable of outputting a control signal corresponding to on/off states of the first driving device 511 according to a position of the diagnosis part 20 detected by the first sensor 512. For example, when the first sensor 512 is implemented as a traction motor, the first sensor 512 may detect a position of a magnet included in a rotor and the number of rotations of a rotor core in the rotor. In this case, for example, a threshold position of the magnet in the rotor and a threshold rotation number of the rotor core therein may be preset in the first limit switch 513. When the first sensor 512 detects that the position of the magnet in the rotor and the number of rotations of the rotor core therein respectively reach their threshold values, the first limit switch 513 may forcibly stop an operation of the first driving device 511. Accordingly, generation of a driving force by the first driving device 511 may be stopped, movement of the first connector 21 that receives a driving force from the first driving device 511 may be stopped, and relative positions of the diagnosis part 20 and the main body 25 connected by the first connector 21 may be fixed.

According to an embodiment, the second driving unit 520 may include a second driving device 521 that is positioned between the ultrasound diagnosis device 30 and the main body 25 to transmit a driving force to a second connector 31 connecting between the ultrasound diagnosis device 30 and the main body 25, a second sensor 522 capable of detecting a change in a position of the ultrasound diagnosis device 30 due to a driving force generated by the second driving device 521, and a second limit switch 523 capable of stopping driving by the second driving device 521 in a critical condition. Because the second driving unit 520 has substantially the same configuration as the first driving unit 510, a detailed description thereof will be omitted here for convenience.

Referring to FIGS. 4A and 4B, the diagnosis part 20 and the ultrasound diagnosis device 30 may be arranged in different directions with respect to the chair unit 400. However, embodiments of the present disclosure are not limited thereto, and the diagnosis part 20 and the ultrasound diagnosis device 30 may be arranged in the same direction with respect to the chair unit 400 or may be formed integrally with each other. For example, a probe holder may be provided on one side 22 of the diagnosis part 20 as shown in FIG. 2, and accordingly, the ultrasound probe 310 may also be placed on the one side 22 of the diagnosis part 20.

According to an embodiment, the diagnosis part 20, the ultrasound diagnosis device 30, and the chair unit 400 may move to specific positions where user convenience may be provided according to a diagnostic mode, as described below with reference to FIGS. 7A through 10C. In this case, when the diagnosis part 20 or the ultrasound diagnosis device 30 interfere with a body of the object positioned on the chair unit 400 for examination, such interference may unintentionally cause damage to the body of the object and the medical diagnosis apparatus 1. Thus, the diagnosis part 20 and the ultrasound diagnosis device 30 may be arranged to be spaced apart from the chair unit 400 by more than a predetermined range such that they may not interfere with the body of the object.

For example, when the diagnosis part 20 and the ultrasound diagnosis device 30 are arranged in different directions with respect to the chair unit 400 as shown in FIG. 4A, the diagnosis part 20 may be spaced apart from a center line O along a length direction of the chair unit 400 by a first distance $T_1$ between the center line O and a center line $M_1$ of the diagnosis part 20 extending along a direction parallel to the center line O, e. g., by a distance of 40 cm to 90 cm, according to a diagnostic state of the object. For example, in this case, a width $W_2$ of the diagnosis part 20 perpendicular to the center line O may be in a range of 30 cm to 60 cm, while a width $W_1$ of the chair unit 400 perpendicular to the center line O may be in a range of 40 cm to 110 cm. Although FIG. 4A shows the width $W_1$ of the chair unit 400 measured with respect to the seat 410, embodiments of the present disclosure are not limited thereto, and the width $W_1$ of the chair unit 400 may be a distance between two ends of the first and second rests 431 and 432 according to positions of the diagnosis part 20 and the ultrasound diagnosis device 30, which vary depending on a diagnostic state of the object. The probe holder 330 included in the ultrasound diagnosis device 30 may also be spaced apart from the center line O along the length direction of the chair unit 400 by a second distance $T_2$ between the center line O and a center line $M_2$ of the probe holder 330 extending along a direction parallel to the center line O, e. g., by a distance of 35 cm to 85 cm, according to a diagnostic state of the object. For example, in this case, a width $W_3$ of the probe holder 330 perpendicular to the center line O may be in a range of 20 cm to 40 cm, while the width $W_1$ of the chair unit 400 perpendicular to the center line O may be in a range of 40 cm to 110 cm.

Furthermore, as shown in FIG. 4B, the diagnosis part 20 may be arranged such that a lower end of the diagnosis part 20 is spaced apart from the seat 410 included in the chair unit 400 by a first height $h_1$ in a Z-axis direction, e.g., by a height of 5 cm to 70 cm, according to a diagnostic state of the object. The probe holder 330 included in the ultrasound diagnosis device 30 may also be arranged such that a lower end of the probe holder 330 is spaced apart from the seat 410 included in the chair unit 400 by a second height $h_2$ in the Z-axis direction, e. g., by a height of 5 cm to 70 cm, according to a diagnostic state of the object.

According to an embodiment, the diagnosis part 20 and the ultrasound diagnosis device 30 may receive driving forces respectively from the first and second driving device 511 and 521 shown in FIG. 3 so as to move. Thus, states in which the first and second driving devices 511 and 521 generate driving forces may respectively be set to correspond to ranges of the predetermined distances $T_1$ and $T_2$ and predetermined heights $h_1$ and $h_2$ such that the diagnosis part 20 and the ultrasound diagnosis device 30 may not interfere with the chair unit 400 and the body of the object. When the first and second sensors 512 and 522 detect that positions of the diagnosis part 20 and the ultrasound diagnosis device 30 respectively deviate from the ranges of the predetermined distances $T_1$ and $T_2$ and predetermined heights $h_1$ and $h_2$, which are set such that the diagnosis part 20 and the ultrasound diagnosis device 30 may not interfere with the chair unit 400 and the body of the object, the first and second limit switches 513 and 523 may respectively forcibly stop driving operations by the first and second driving devices 511 and 521, and accordingly, may prevent damage to the body of the object and the medical diagnosis apparatus 1 due to interference between the object and the diagnosis part 20 and the ultrasound diagnosis device 30.

Figure 5A:
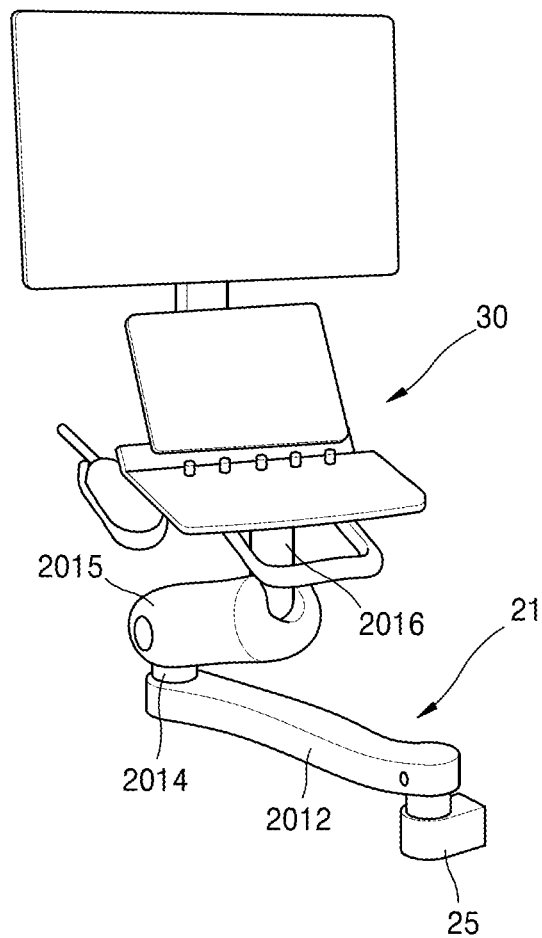
FIG. 5A is a perspective view of a first connector according to an embodiment.
Figure 5B:
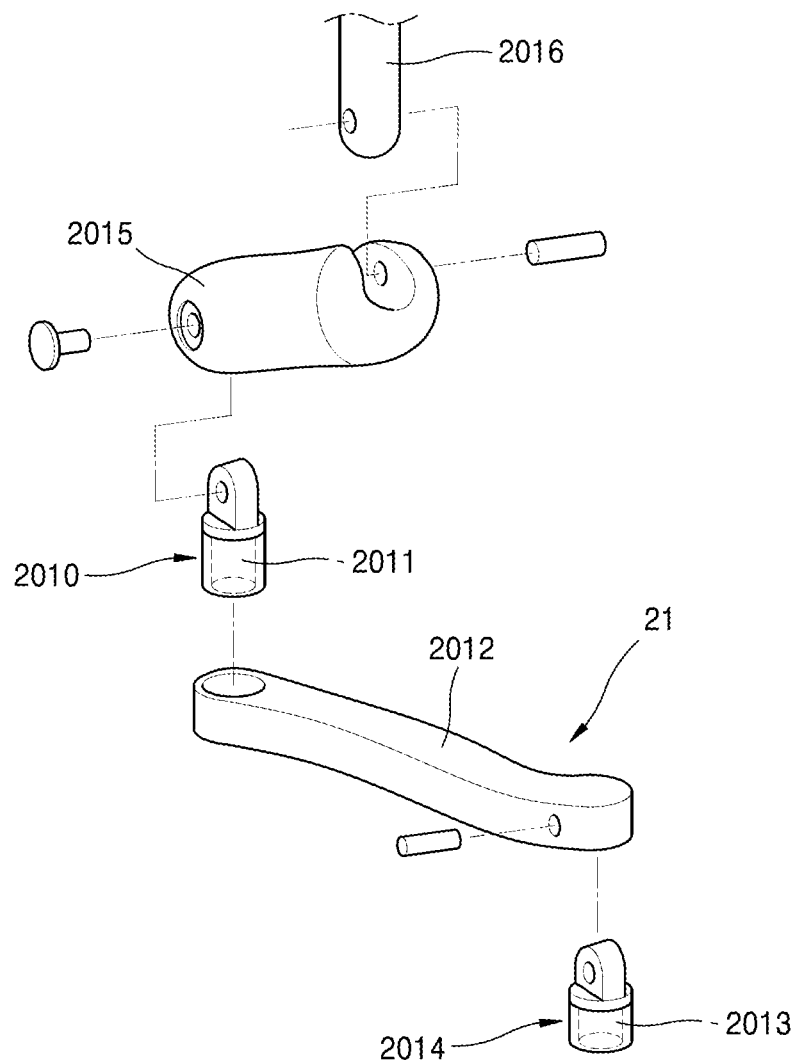
FIG. 5B is an exploded perspective view of a first connector according to an embodiment.
Figure 5C:
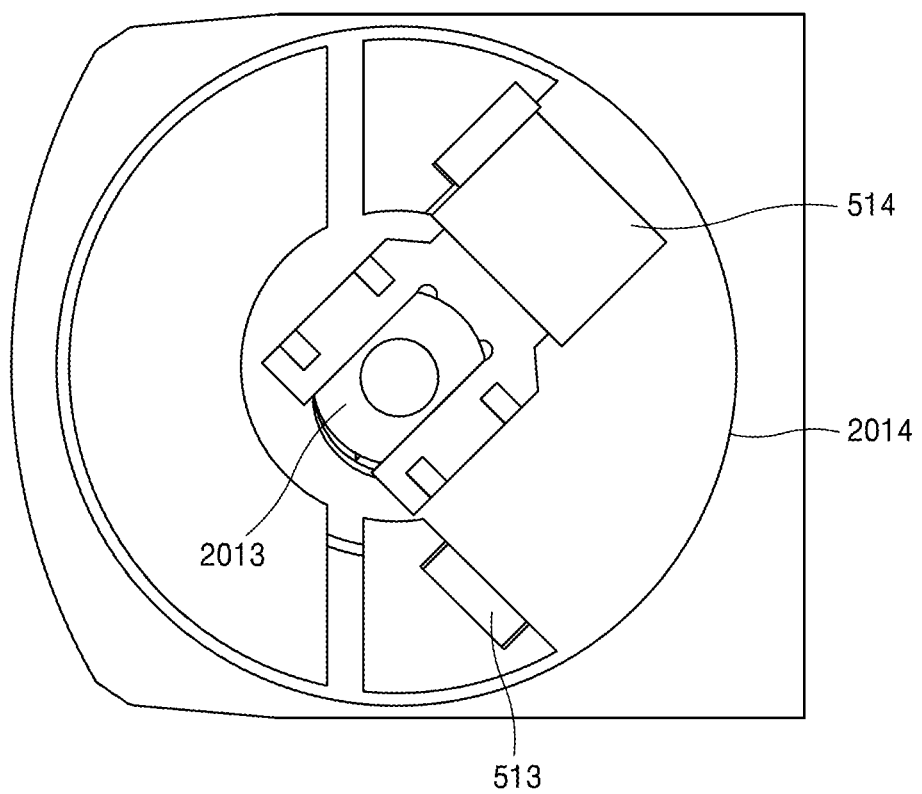
FIG. 5C is a schematic diagram of a rotation axis and a limit switch according to an embodiment.
Figure 5D:
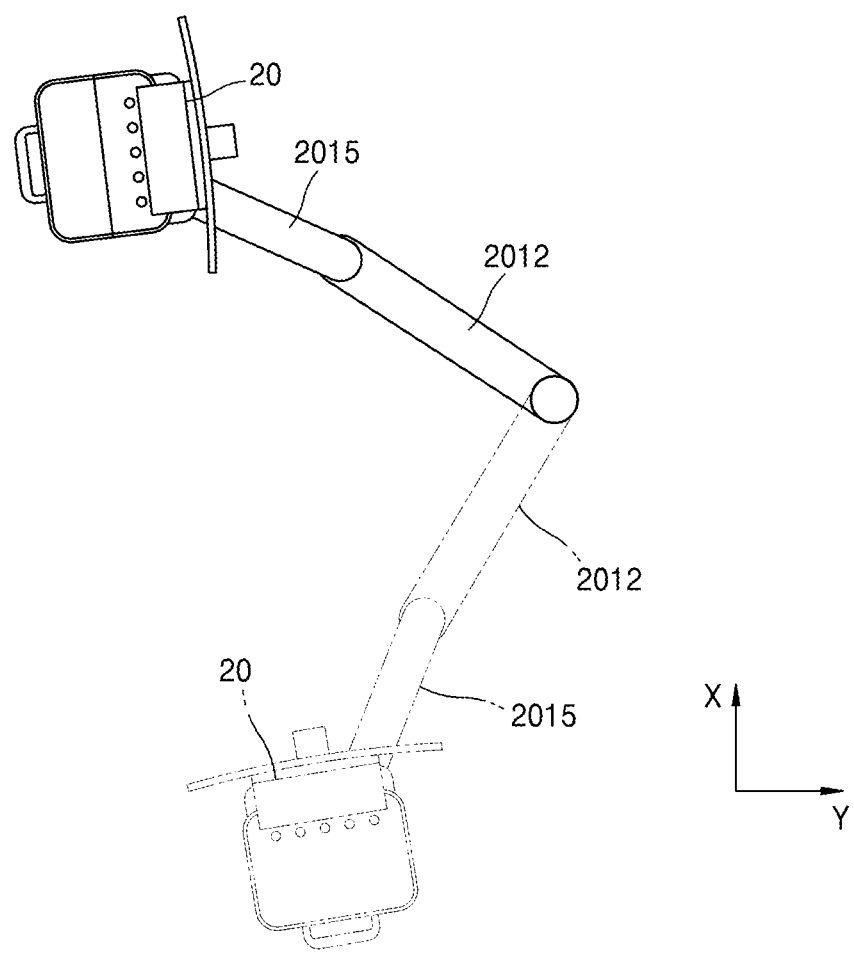
FIG. 5D is a plan view of a first connector according to an embodiment.
Figure 5E:
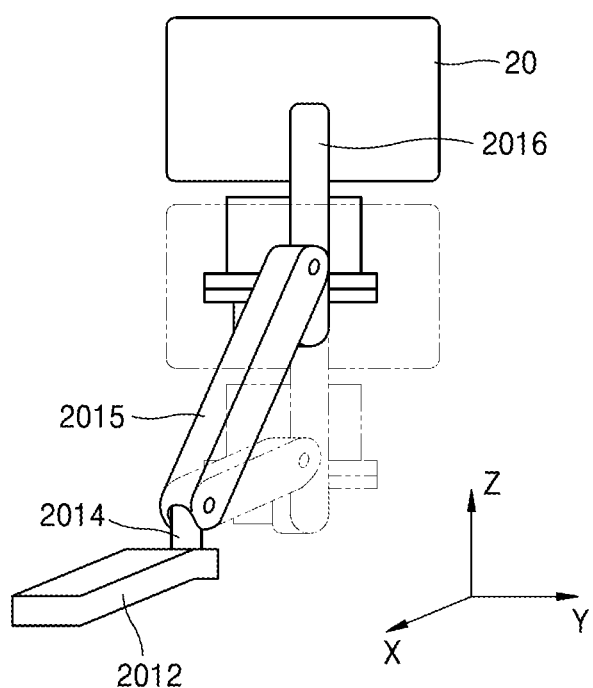
FIG. 5E is a side view of a first connector according to an embodiment.

FIG. 5A is a perspective view of a first connector according to an embodiment. FIG. 5B is an exploded perspective view of the first connector according to an embodiment. FIG. 5C is a schematic diagram of a rotation axis and a limit switch according to an embodiment. FIG. 5D is a plan view of a first connector according to an embodiment. FIG. 5E is a side view of a first connector according to an embodiment.

As described above, according to an embodiment, the diagnosis part 20 and the ultrasound diagnosis device 30 may move to specific positions according to diagnostic states. The driver 50 shown in FIG. 1 may generate driving forces according to a control signal received from the controller 250 and respectively transmit the driving forces to the first and second connectors 21 and 31, each being implemented as a plurality of link parts, such that the diagnosis part 20 and the ultrasound diagnosis device 30 may be automatically arranged at predetermined diagnostic positions corresponding to each diagnostic state.

According to an embodiment, as shown in FIGS. 5A and 5B, the first connector 21 may include a first engaging member 2010 coupled to the main body 25 to be rotatable around a first rotation axis 2011 and a first arm 2012 hinged with the first engaging member 2010, a second engaging member 2014 coupled to one end of the first arm 2012 to be rotatable around a second rotation axis 2013 and a second arm 2015 hinged with the second engaging member 2014, and a connection member 2016 having one end coupled to the diagnosis part 20 and the other end hinged to one end of the second arm 2015 and connecting the diagnosis part 20 to the second arm 2015.

Referring to FIG. 5D, the diagnosis part 20 may be connected to the main body 25 by the first and second arms 2012 and 2015. For example, the first arm 2012 may be rotatably coupled to the main body 25 due to the first rotation axis 2011, and thus, may move in an XY plane to be rotatable about the first rotation axis 2011 with respect to the main body 25. Furthermore, the second arm 2015 may be rotatably coupled to the first arm 2012 due to the second rotation axis 2013, and thus, may move in the XY plane to be rotatable about the second rotation axis 2013 with respect to the first arm 2012. Accordingly, the diagnosis part 20 connected to the main body 25 by the first and second arms 2012 and 2015 may move freely with respect to the main body 25 in one plane (the XY plane).

According to an embodiment, the first and second arms 2012 and 2015 may each receive a driving force from the first driving device 511 of FIG. 3 for rotational movement. In this case, when the first sensor 512 detects that a position of the diagnosis part 20 connected to the first and second arms 2012 and 2015 deviates from a range of the predetermined distance $T_1$ from the chair unit 400, the first limit switch 513 may forcibly stop driving by the first driving device 511.

For example, as shown in FIG. 5C, driving by the first driving device 511 may be forcibly stopped by the first limit switch 513 capable of limiting rotation of the second rotation axis 2013. According to an embodiment, one or a plurality of first limit switches 513 may be arranged on a path of rotation of the second rotation axis 2013 in order to limit a range of rotation of the second rotation axis 2013, and may contact a damper fixedly attached to the second rotation axis 2013 to limit rotation of the second rotation axis 2013 and thus rotation of the second arm 2015 connected to the second rotation axis 2013, thereby preventing interference between the diagnosis part 20 and the object. However, a configuration of a limit switch is not limited thereto, and the limit switch may be implemented as a control member capable of limiting rotations of the first and second rotation axes 2011 and 2013 with respect to the first and second arms 2012 and 2015 when the first and second arms 2012 and 2015 move beyond their movable ranges.

Referring to FIGS. 5B and 5E, according to an embodiment, the diagnosis part 20 may be connected to the main body 25 by the first and second arms 2012 and 2015 and the connection member 2016. For example, the first arm 2012 may be hinged to the main body 25, and the second arm 2015 may be hinged to the first arm 2012 and the connection member 2016. Accordingly, the second arm 2015 may move up and down with respect to the first arm 2012 along the Z-axis direction. Thus, the diagnosis part 20 connected to the main body 25 by the first and second arms 2012 and 2015 and the connection member 2016 may move up and down with respect to the main body 25 along the Z-axis direction. In this case, when the second arm 2015 rotates such that the diagnosis part 20 moves up and down outside a range of the predetermined first height $h_1$ as shown in FIG. 4B, the first limit switch 513 may forcibly stop driving by the first driving device 511 to thereby prevent interference between the object and the diagnosis part 20. Because the second connector 31 for connecting the ultrasound diagnosis device 30 to the main body 25 has substantially the same configuration as the first connector 21, a detailed description thereof will be omitted here for convenience.

Figure 6:
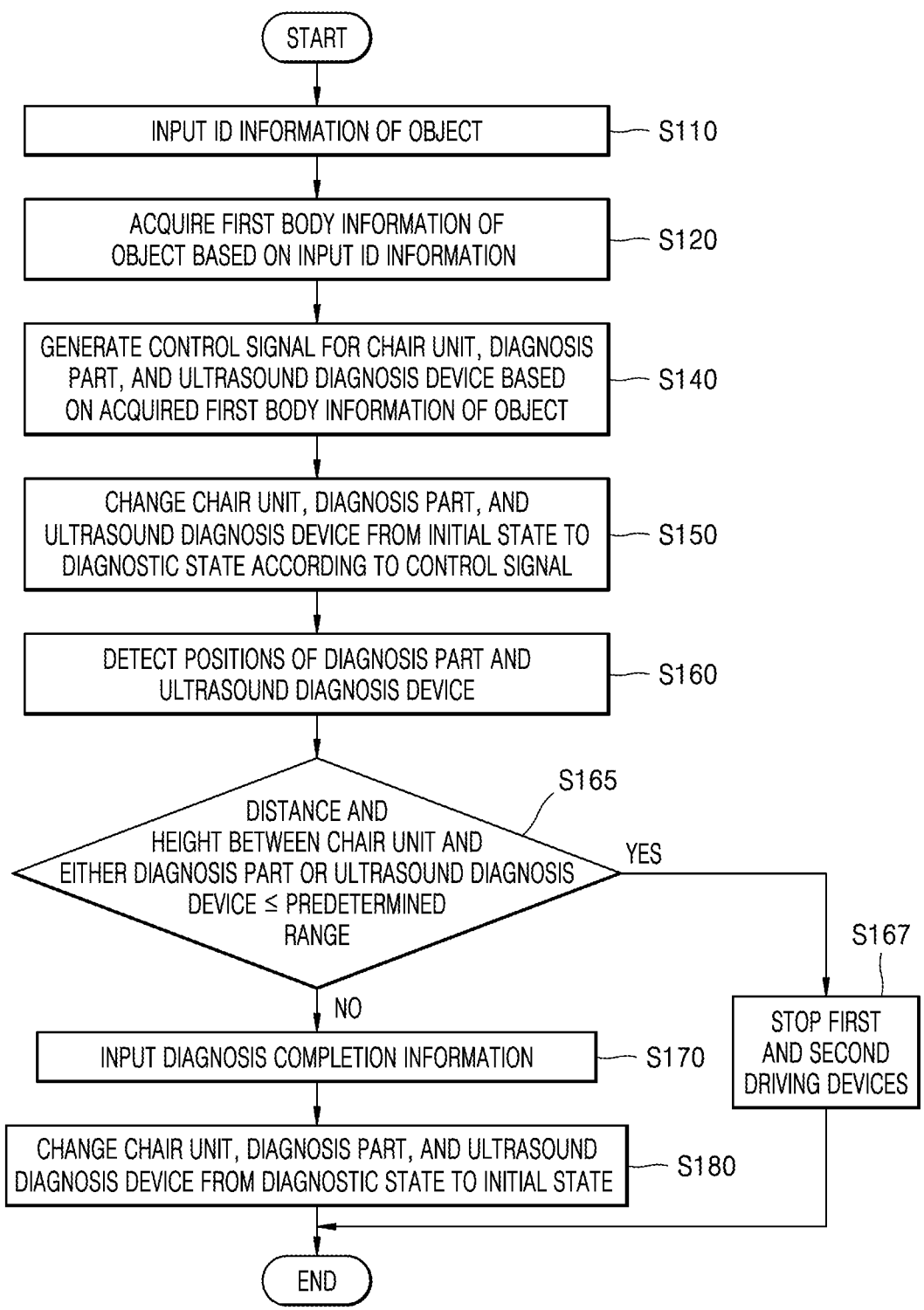
FIG. 6 is a flowchart of a diagnosis method using a medical diagnosis apparatus, according to an embodiment.
Figure 7A:
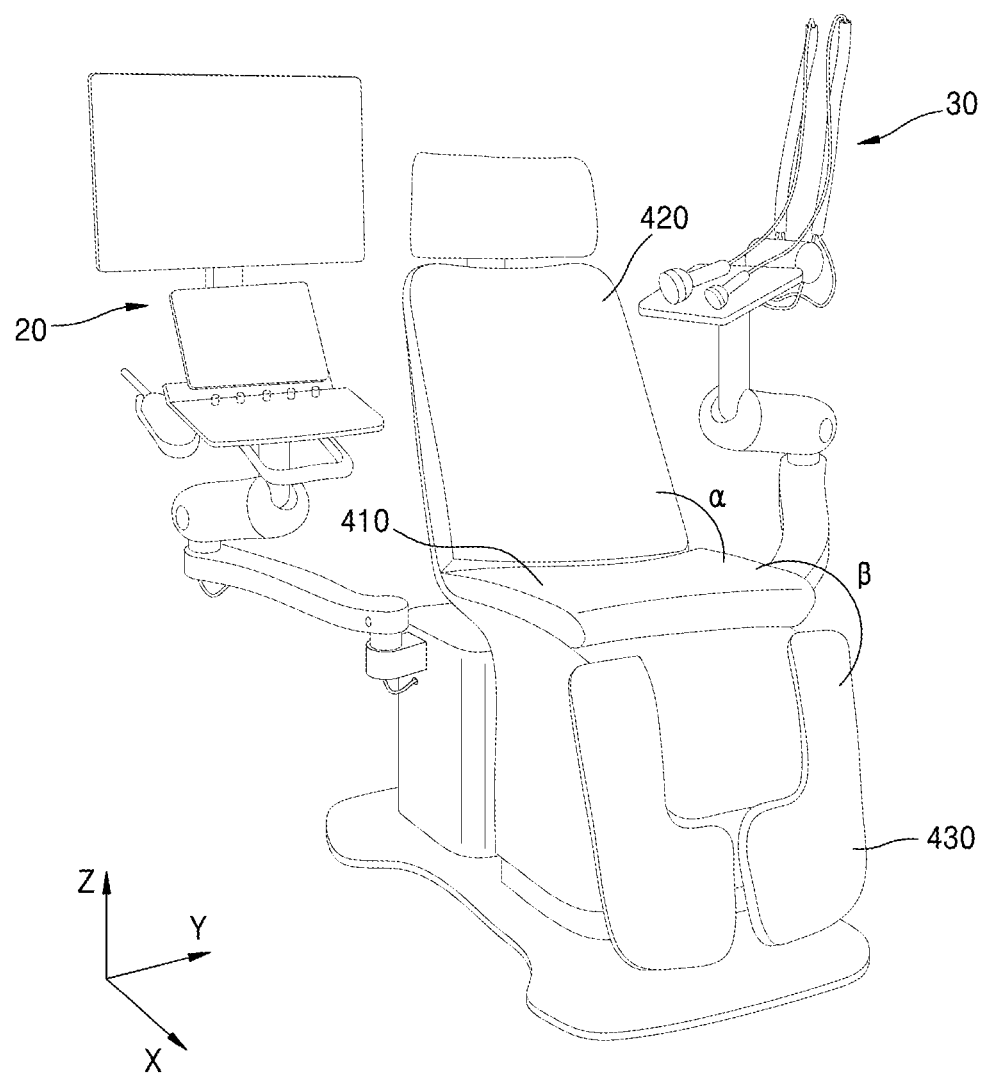
FIGS. 7A through 7C are respectively a perspective view, a side view, and a plan view of a medical diagnosis apparatus that is in an initial state, according to an embodiment.
Figure 7B:
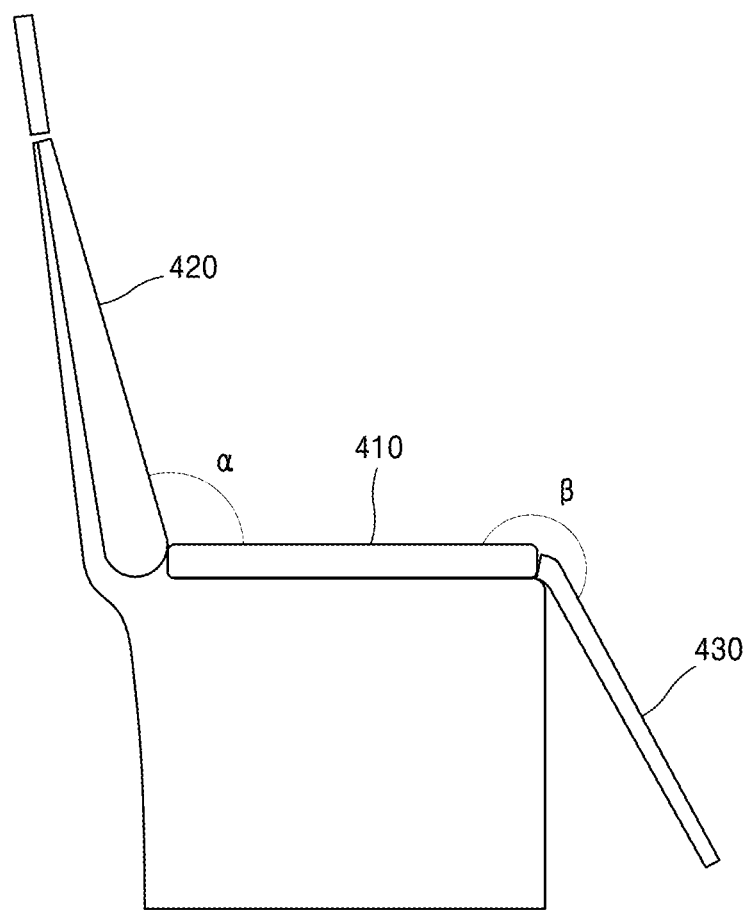
Figure 7C:
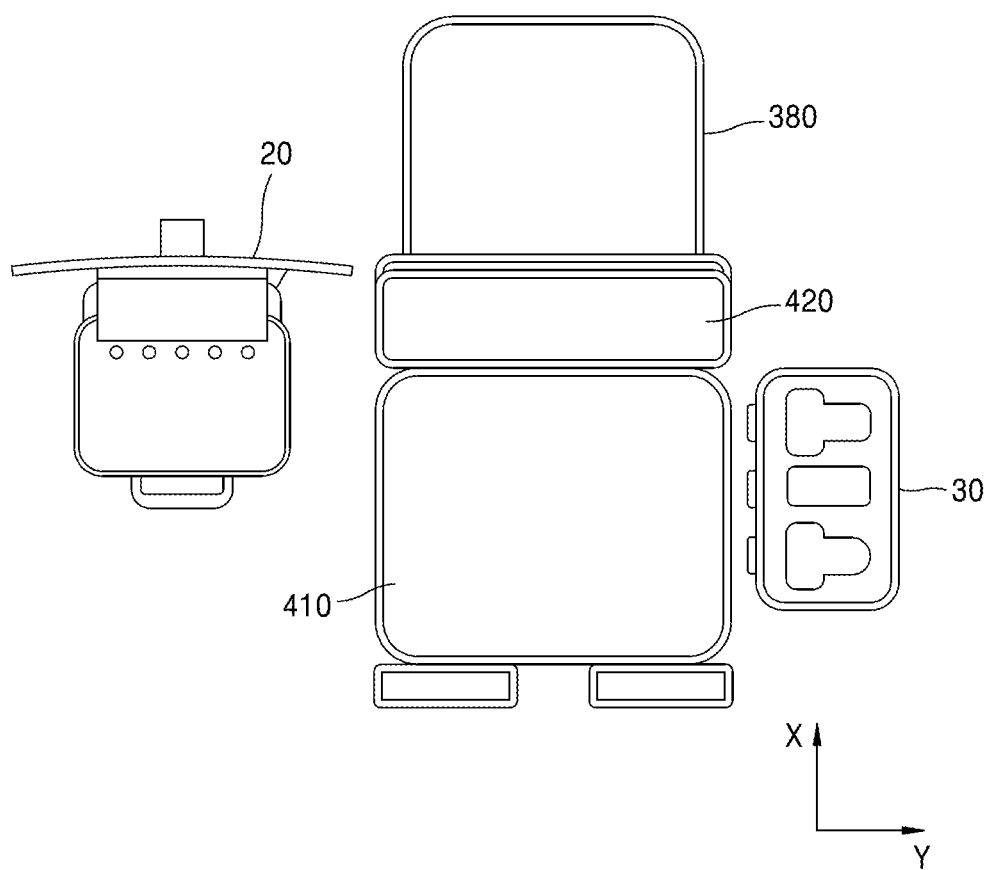
Figure 8A:
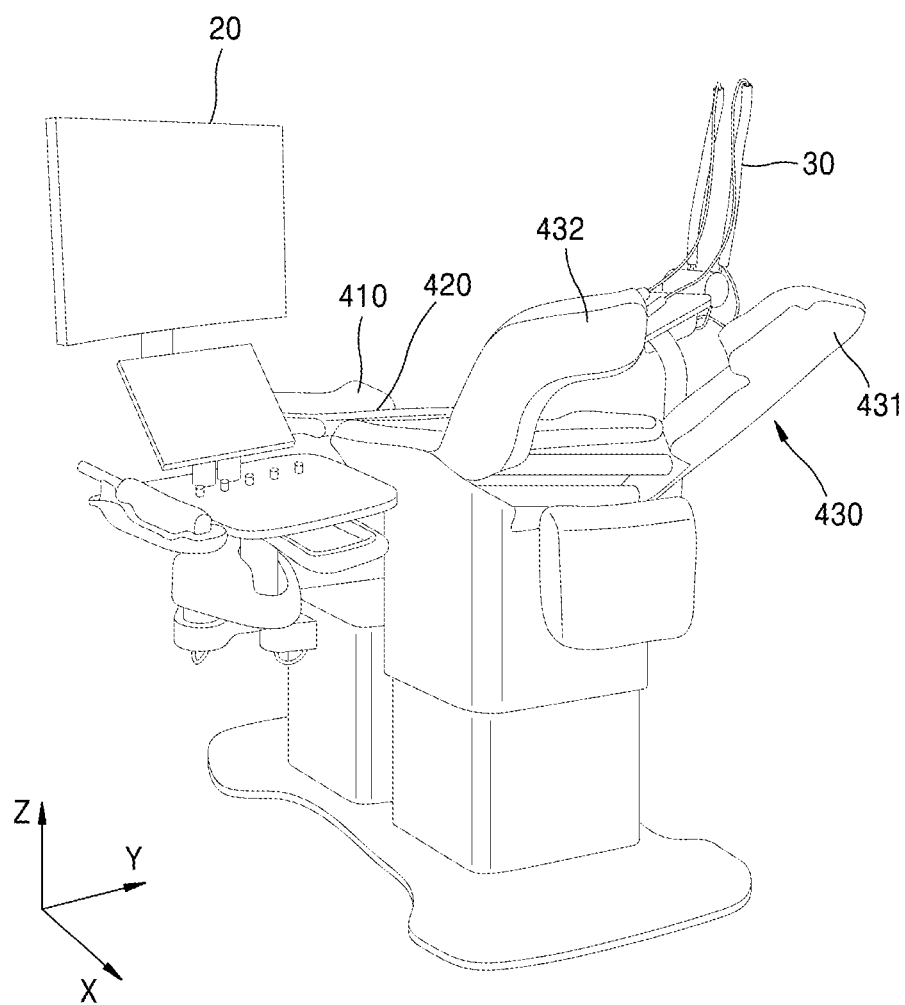
FIGS. 8A through 8C are respectively a perspective view, a side view, and a plan view of a medical diagnosis apparatus that is in a first diagnostic state, according to an embodiment.
Figure 8B:
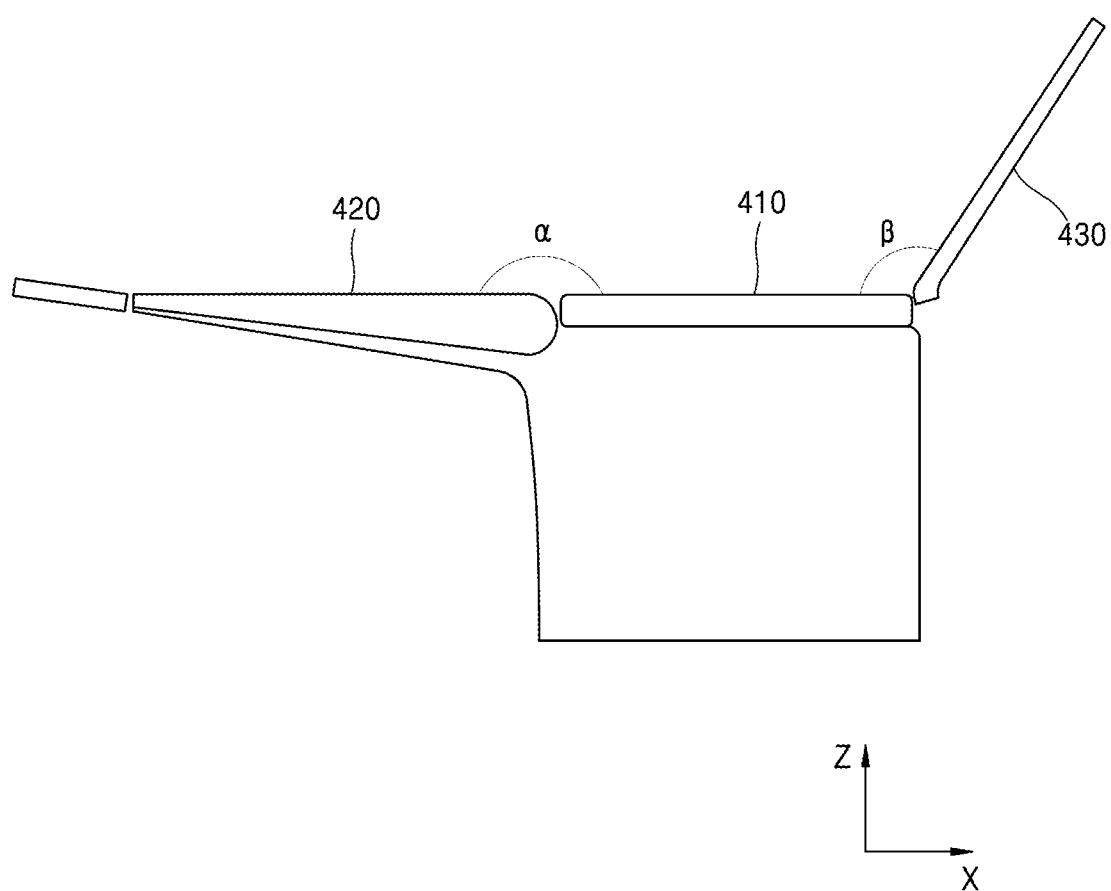
Figure 8C:
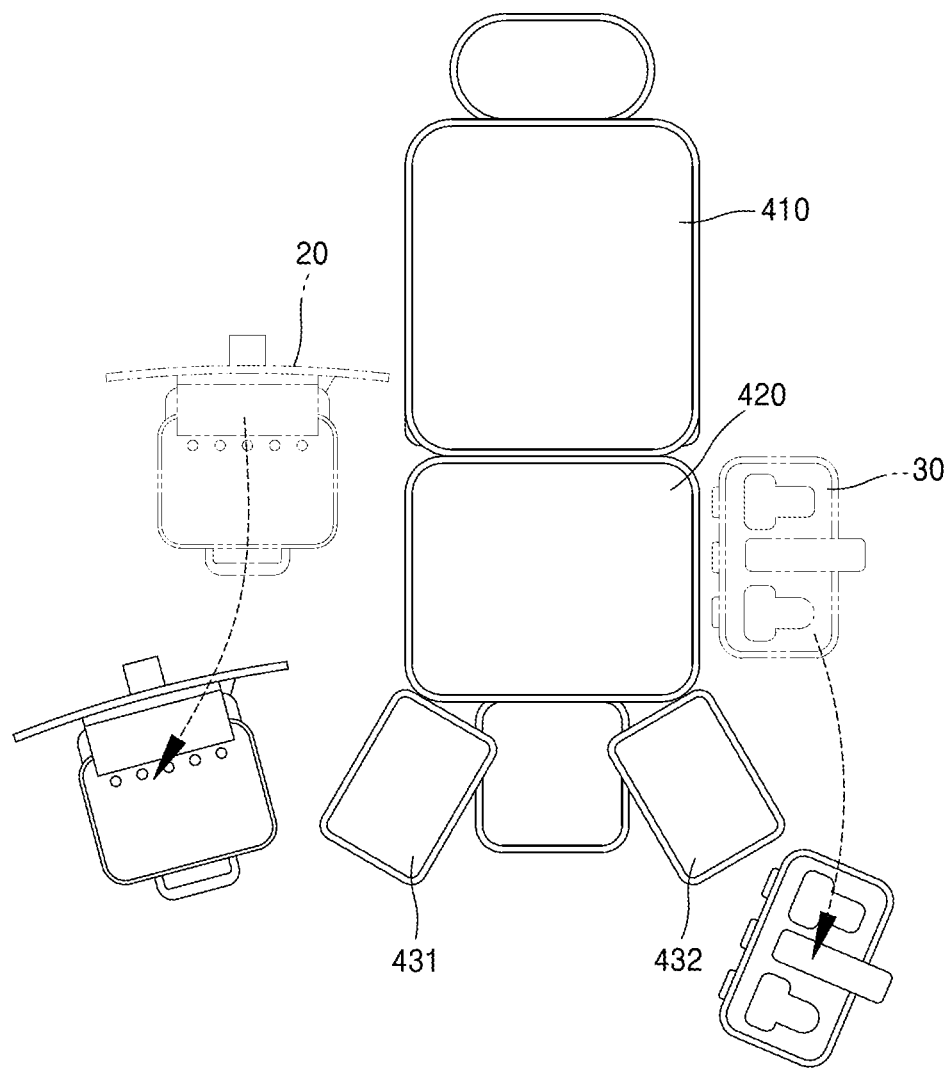
Figure 9A:
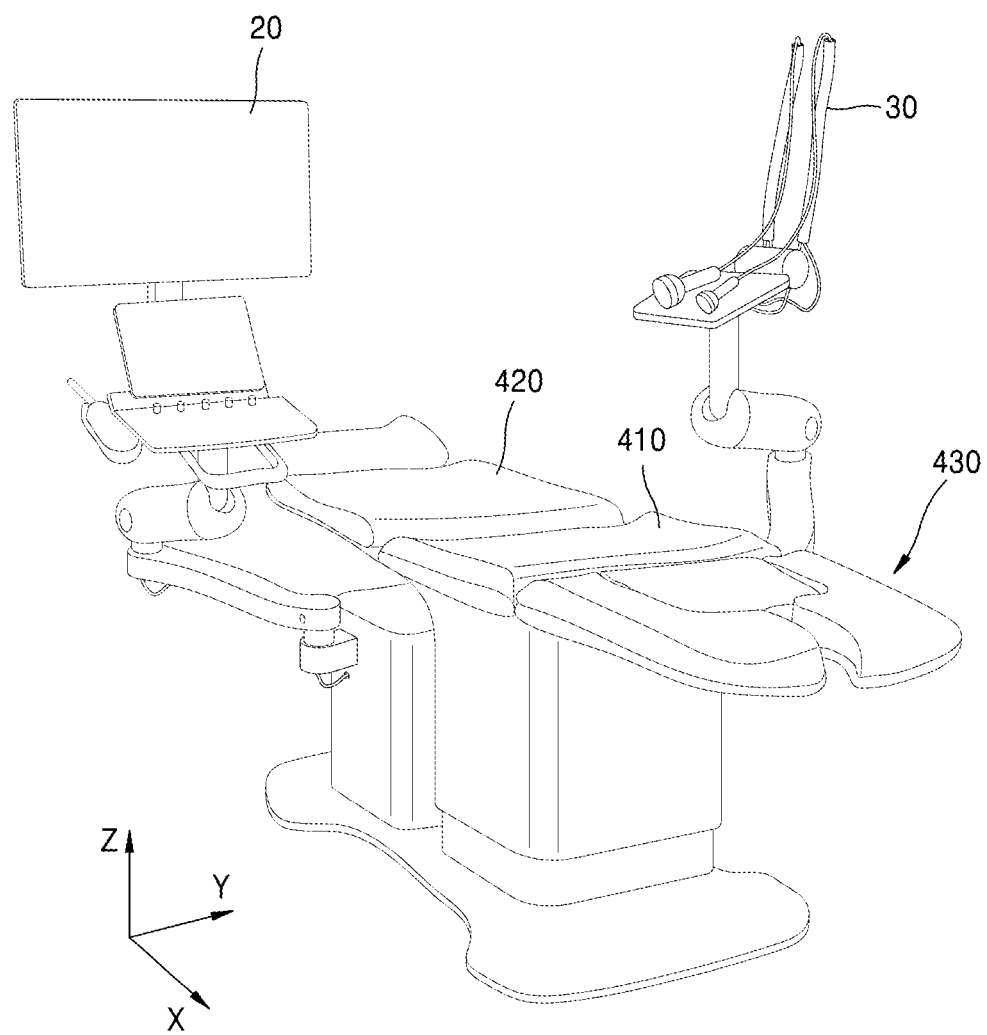
FIGS. 9A and 9B are respectively a perspective view and a plan view of a medical diagnosis apparatus that is in a second diagnostic state, according to an embodiment.
Figure 9B:
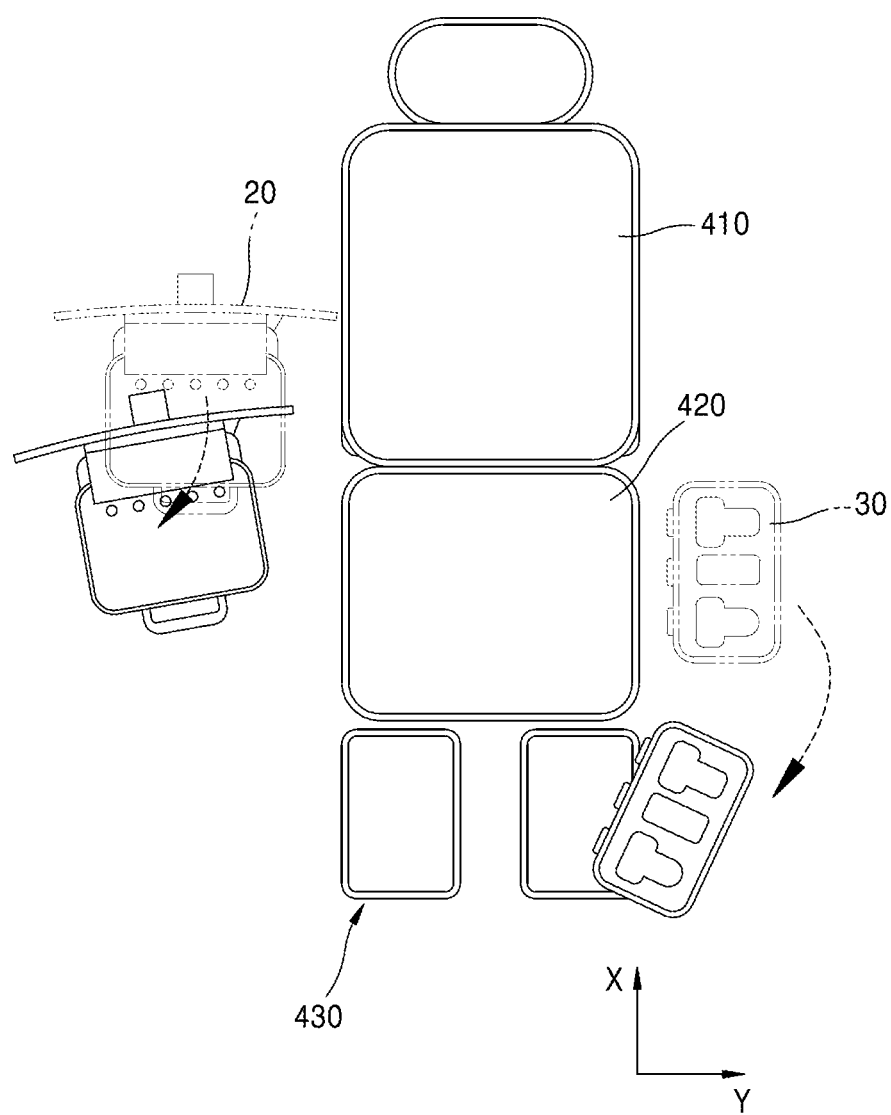
Figure 10A:
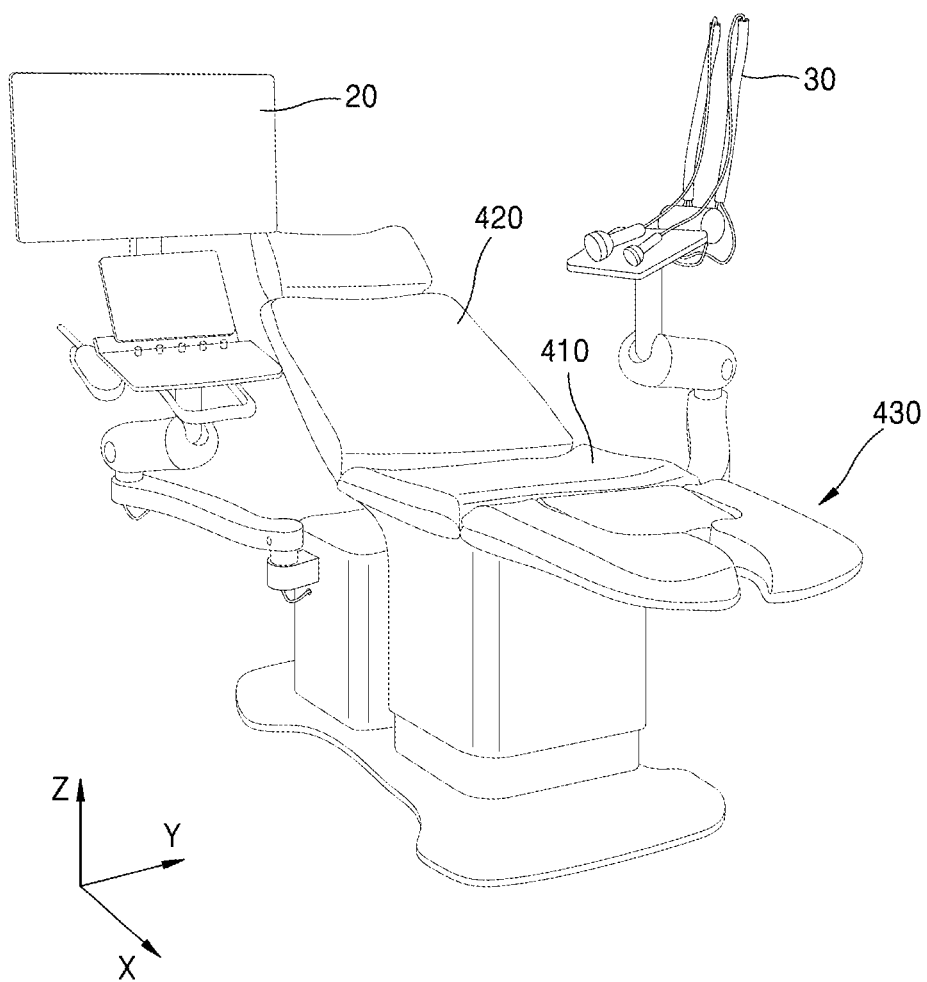
FIGS. 10A through 10C are respectively a perspective view, a side view, and a plan view of a medical diagnosis apparatus that is in a third diagnostic state, according to an embodiment.
Figure 10B:
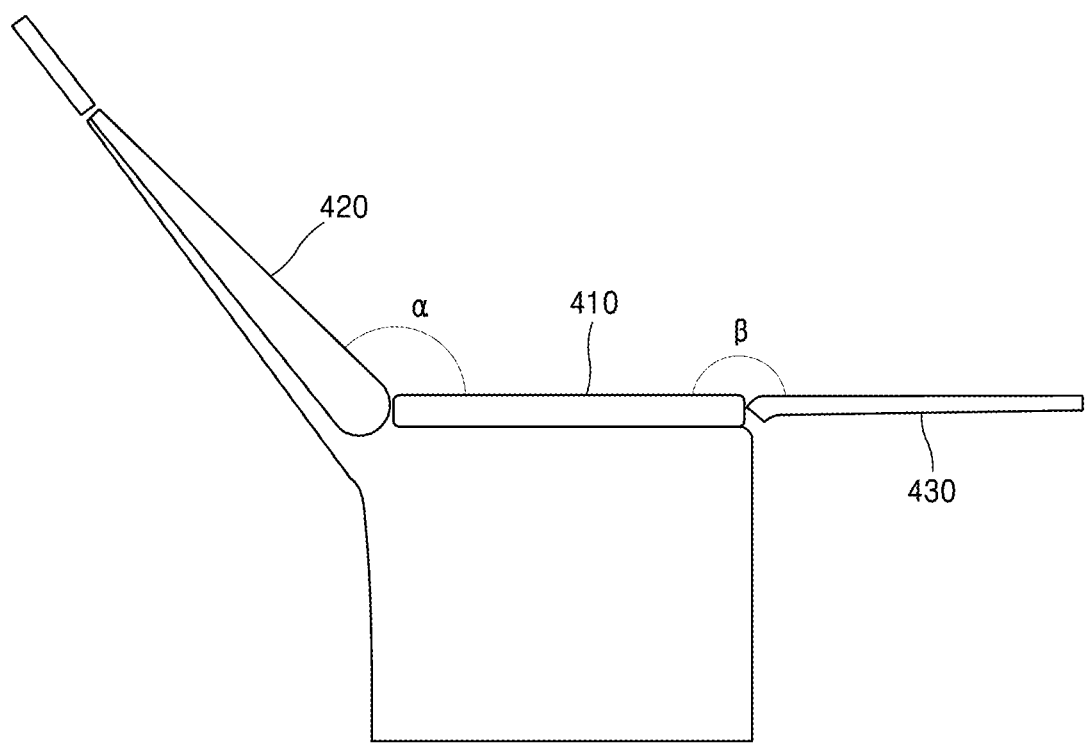
Figure 10C:
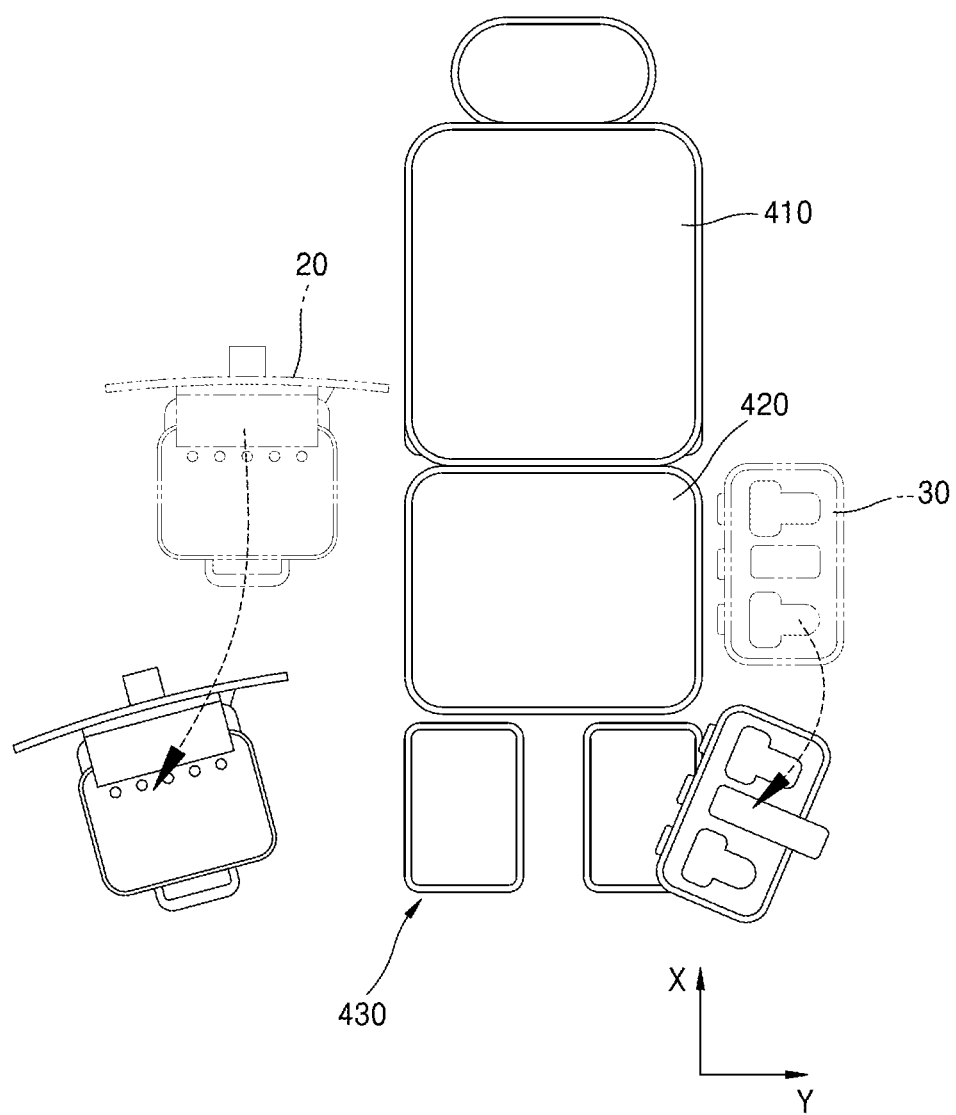

FIG. 6 is a flowchart of a diagnosis method using a medical diagnosis apparatus, according to an embodiment. FIGS. 7A through 7C are respectively a perspective view, a side view, and a plan view of a medical diagnosis apparatus that is in an initial state, according to an embodiment. FIGS. 8A through 8C are respectively a perspective view, a side view, and a plan view of a medical diagnosis apparatus that is in a first diagnostic state, according to an embodiment. FIGS. 9A and 9B are respectively a perspective view and a plan view of a medical diagnosis apparatus that is in a second diagnostic state, according to an embodiment. FIGS. 10A through 10C are respectively a perspective view, a side view, and a plan view of a medical diagnosis apparatus that is in a third diagnostic state, according to an embodiment.

Referring to FIG. 6, in operation S110, ID information of an object is input via the input interface 270 included in the diagnosis part 20. For example, as described above ID information of the object means at least one of all types of information used to identify the object, such as a name, a resident registration number, a birth date, a personal ID number, a personal ID code, and biometric recognition information such as a face, an iris, a fingerprint, etc.

In operation S120, first body information of the object is acquired using the ID information of the object input via the input interface 270. According to an embodiment, the controller 250 may acquire first body information of the object corresponding to the ID information of the object and which is stored in the storage 255 or an external apparatus by using the ID information of the object input via the input interface 270. In this case, the first body information of the object may be stored in the storage 255 included in the diagnosis part 20 or the external apparatus capable of performing communication via the communicator 260. In this case, the first body information of the object means all pieces of prestorable body information of the object for obstetrical and gynecological treatment, such as a pregnant woman's gestational age, the number of fetuses, a fetal position, a pregnant woman's weight, stature, body temperature, examination history, medical history, etc.

In operation S140, a control signal for moving the chair unit 400, the diagnosis part 20, and the ultrasound diagnosis device 30 is generated based on the acquired first body information of the object. According to an embodiment, the controller 250 may identify a diagnostic state of the object and body information thereof by using the acquired first body information of the object. In this case, the chair unit 400, the ultrasound diagnosis device 30, and the diagnosis part 20 may be changed according to a diagnostic state of the object and body information thereof, and the controller 250 generates a control signal that may be used to generate a driving force for changing the shapes of and moving the chair unit 400, the ultrasound diagnosis device 30, and the diagnosis part 20

In operation S150, the chair unit 400, the diagnosis part 20, and the ultrasound diagnosis device 30 are changed from an initial state to a diagnostic state based on a control signal generated by the controller 250. According to an embodiment, the driver 50 may generate a driving force according to a control signal generated by the controller 250 to change the chair unit 400, the diagnosis part 20, and the ultrasound diagnosis device 30 from an initial state to a diagnostic state. For example, the chair unit 400, the diagnosis part 20, and the ultrasound diagnosis device 30 may be changed from an initial state to first through third diagnostic states according to body information of the object such as a gestational age.

According to an embodiment, in an initial state, the chair unit 400 may have a structure that makes it easy for the object to sit thereon as shown in FIGS. 7A through 7C. For example, in the initial state, the upper body support 420 may be arranged to have a first angle α of 90° to 120° with respect to the seat 410 in a counterclockwise direction. Furthermore, in this case, the leg rest 430 may be arranged to have a second angle β of 240° to 360° with respect to the seat 410 in a clockwise direction. Furthermore, the ultrasound diagnosis device 30 and the diagnosis part 20 may be each arranged adjacent to the seat 410 such that they do not interfere with the object while the object is sitting on the chair unit 400 due to operations of the first and second driving devices 511 and 521. In this case, when the distances $T_1$ and $T_2$ or heights $h_1$ and $h_2$ between the chair unit 400 and either the diagnosis part 20 or the ultrasound diagnosis device 30 exceed a predetermined range indicated in FIG. 4A or 4B, the first or second limit switch 513 and 523 may stop driving by the first or second driving device 511 or 521.

Furthermore, according to an embodiment, in a first diagnostic state, when the object, i.e., a pregnant woman, is in an early stage (10 weeks or less of pregnancy), the chair unit 400 may have a structure for diagnosing a lower body part of the object as shown in FIGS. 8A through 8C. For example, in the first diagnostic state, the upper body support 420 may be tilted to lie flat with respect to the seat 410, i.e., to have a first angle α of 180° with respect to the seat 410. However, embodiments of the present disclosure are not limited thereto, and the upper body support 420 may be tilted at a first angle α, e.g., at an angle of 110° to 180°, with respect to the seat 410 when needed during a diagnostic process. Furthermore, the leg rest 430 may be arranged to have a second angle β of 120° to 180° with respect to the seat 410 in a clockwise direction. Furthermore, the seat 410 may be tilted to have an angle of 0° to 20° with respect to the ground.

Furthermore, in this case, the chair unit 400 may be arranged to be raised from or lowered to the ground according to a user's height and a diagnosis type. Furthermore, for example, the ultrasound diagnosis device 30 and the diagnosis part 20 may be raised from or lowered to the ground according to a user's height or a diagnosis type, and may be arranged adjacent to the leg rest 430 by moving away from the seat 410 based on a user's arm length and a diagnosis type, thereby maximizing usage convenience of the user. Furthermore, the diagnosis part 20 and the ultrasound diagnosis device 30 may be each arranged adjacent to the leg rest 430 due to the first and second driving devices 511 and 521, thereby providing user convenience in the first diagnostic state. In this case, when the diagnosis part 20 and the ultrasound diagnosis device 30 are arranged adjacent to the chair unit 400 within a predetermined range, the first or second limit switch 513 or 523 may stop driving by the first or second driving device 511 or 521 in substantially the same manner as in the initial state, and thus, a description thereof will be omitted here.

Furthermore, according to an embodiment, in a second diagnostic state, when the object, i.e., the pregnant woman, is in a middle stage (10 to 30 weeks of pregnancy), the chair unit 400 may have a structure for diagnosing an abdominal part of the object as shown in FIGS. 9A and 9B. For example, in the second diagnostic state, the seat 410, the upper body support 420, and the leg rest 430 may be arranged in one plane. In other words, the upper body support 420 may be tilted to lie flat with respect to the seat 410, i.e., to have a first angle α of 180° with respect to the seat 410. However, embodiments of the present disclosure are not limited thereto, and the upper body support 420 may be tilted at a first angle α, e. g., at an angle of 110° to 180°, with respect to the seat 410 when needed during a diagnostic process. Because matters related to raising and lowering of the chair unit 400 and movements of the diagnosis part 20 and the ultrasound diagnosis device 30 based on a user's height and a diagnosis type are substantially the same as those in the first diagnostic state, detailed descriptions thereof will be omitted here. Furthermore, the diagnosis part 20 may be located adjacent to the seat 410 due to the first driving device 511, and the ultrasound diagnosis device 30 may be located adjacent to the leg rest 430 due to the second driving device 521, thereby providing user convenience in the second diagnostic state. In this case, when the diagnosis part 20, the ultrasound diagnosis device 30, and the chair unit 400 are arranged adjacent to one another within a predetermined range, the first or second limit switch 513 or 523 may stop driving by the first or second driving device 511 or 521 in substantially the same manner as in the initial state, and thus, descriptions thereof will be omitted here.

In addition, according to an embodiment, in a third diagnostic state, when the object, i.e., the pregnant woman, is in a late stage (30 weeks or more of pregnancy), the chair unit 400 may have a structure for diagnosing an abdominal part of the object as shown in FIGS. 10A through 10C. When the pregnant woman enters the late stage of pregnancy, it may be hard for her to lie flat on her back due to a fetal weight. Thus, the upper body support 420 needs to move relative to the seat 410 by taking into account diagnostic convenience for the object. For example, in the third diagnostic state, the upper body support 420 may be tilted to have a first angle α of 110° to 170° with respect to the seat 410 in a counterclockwise direction. Furthermore, the leg rest 430 may be arranged in the same plane as the seat 410. Because matters related to raising and lowering of the chair unit 400 and movements of the diagnosis part 20 and the ultrasound diagnosis device 30 based on a user's height and a diagnosis type are substantially the same as those in the first diagnostic state, detailed descriptions thereof will be omitted here. Furthermore, the diagnosis part 20 and the ultrasound diagnosis device 30 may be each arranged adjacent to the leg rest 430 due to the first and second driving devices 511 and 521, thereby providing user convenience in the third diagnostic state. In this case, when the diagnosis part 20, the ultrasound diagnosis device 30, and the chair unit 400 are arranged adjacent to one another within a predetermined range, the first or second limit switch 513 or 523 may stop driving by the first or second driving device 511 or 521 in substantially the same manner as in the initial state, and thus, descriptions thereof will be omitted here.

In operation S160, positions of the diagnosis part 20 and the ultrasound diagnosis device 30, which vary depending on driving forces generated by the first and second driving devices 511 and 521, are detected. For example, as shown in FIG. 3, the first sensor 512 may detect a position of the diagnosis part 20, which varies depending on a driving force generated by the first driving device 511, and the second sensor 522 may detect a position of the ultrasound diagnosis device 30, which varies depending on a driving force generated by the second driving device 521.

In operation S165, it may be determined, based on the detected positions of the diagnosis part 20 and the ultrasound diagnosis device 30, whether a distance or height between the chair unit 400 and either the diagnosis part 20 or the ultrasound diagnosis device 30 is in a range that is less than or equal to a predetermined range. For example, when a distance or height between the chair unit 400 and either the diagnosis part 20 or the ultrasound diagnosis device 30 is in a range that is less than or equal to a predetermined range, interference may occur between the object and the diagnosis part 20 and the ultrasound diagnosis device 30 and cause damage to the object and the medical diagnosis apparatus 1. For example, to prevent such damage to the object and the medical diagnosis apparatus 1, the first and second sensors 512 and 522 may continuously detect driving states of the first and second driving devices 511 and 521, respectively.

In operation S167, when the distance or height between the chair unit 400 and either the diagnosis part 20 or the ultrasound diagnosis device 30 is in a range that is less than or equal to the predetermined range, driving by the first and second driving devices 511 and 521 may be stopped. For example, when driving states of the first and second driving devices 511 and 521 reach preset threshold values such that a range of a distance or height between the chair unit 400 and either the diagnosis part 20 or the ultrasound diagnosis device 30 is narrowed down to less than or equal to the predetermined range, the first and second limit switches 513 and 523 shown in FIG. 3 may be respectively used to forcibly stop driving by the first and second driving devices 511 and 521.

In operation S170, when diagnosis of the object by a user is completed, diagnosis completion information is input. According to an embodiment, when diagnosis of the object by the user is completed, the user may hold the ultrasound probe 310 on the probe holder 330. When the probe sensor 331 detects that the ultrasound probe 310 has been held on the probe holder 330 for a certain period of time, it may be recognized that the diagnosis of the object is completed, and diagnosis completion information indicating that the diagnosis of the object is completed may be input. However, embodiments of the present disclosure are not limited thereto, and the diagnosis completion information may be directly input by the user via the input interface 270.

In operation S180, when the diagnosis completion information is input, the chair unit 400, the diagnosis part 20, and the ultrasound diagnosis device 30 are changed from a diagnostic state to an initial state based on a control signal generated by the controller 250. According to an embodiment, the driver 50 may generate a driving force according to a control signal generated by the controller 250 to change the chair unit 400, the diagnosis part 20, and the ultrasound diagnosis device 30 from the diagnostic state to the initial state.

While medical diagnosis apparatuses and medical diagnosis methods using the same have been particularly shown and described with reference to embodiments thereof, it will be understood by those of ordinary skill in the art that the above-described embodiments are merely examples and are intended to cover various changes in form and details and other equivalent embodiments. Accordingly, the true scope of technical protection of the present disclosure will be defined by the technical spirit of the following claims.

The invention claimed is:
1. A medical diagnosis apparatus comprising:
a main body;
a chair unit attached to the main body and movably supported by the main body and on which an object is able to be positioned;
a diagnosis part including a display that is attached to the main body and movably connected to the main body and is spaced apart from the chair unit by a preset first distance in one plane;
a controller configured to generate a control signal for moving the diagnosis part according to preset information; and
a first driving device configured to generate a driving force for moving the diagnosis part according to the control signal, wherein the chair unit and the diagnosis part are spaced apart from each other by a preset first height along a direction perpendicular to the one plane, and the medical diagnosis apparatus further comprises:
- a first sensor configured to detect a position of the diagnosis part, which varies depending on the driving force generated by the first driving device, and
- a first limit switch configured to stop the first driving device as the diagnosis part and the chair unit are arranged adjacent to each other with a distance or height therebetween that is less than or equal to the preset first distance or the preset first height.

2. The medical diagnosis apparatus of claim 1, wherein the first distance that is a distance between a center line in a longitudinal direction of the chair unit and a center line of the diagnosis part extending in a direction parallel to the center line is in a range of 40 cm to 90 cm.

3. The medical diagnosis apparatus of claim 1, wherein the chair unit comprises an upper body support, a seat, and a leg rest sequentially arranged in one direction and connected to one another, and
wherein the first height between the seat and a lower end of the diagnosis part is in a range of 5 cm to 70 cm.

4. The medical diagnosis apparatus of claim 1, wherein the preset information comprises first body information of the object,
the medical diagnosis apparatus further comprising:
- a storage storing the first body information of the object; and
- an input interface configured to input identification information of the object,
wherein the controller is configured to identify the first body information of the object by the identification information of the object, and the identification information of the object includes at least one of name information of the object, fingerprint information of the object, face information of the object, and an identification code corresponding to the object.

5. The medical diagnosis apparatus of claim 4, wherein when the medical diagnosis apparatus is an obstetrical and gynecological diagnosis apparatus, the first body information of the object includes at least one of a gestational age, the number of fetuses, a fetal position, a weight, a height, a body temperature, an examination history, and a medical history.

6. The medical diagnosis apparatus of claim 1, further comprising a first connector that connects the diagnosis part to the main body and is configured such that the diagnosis part is movable with respect to the main body,
wherein the first connector comprises:
- a first engaging member rotatably coupled to the main body;
- a first arm that extends in one direction and is hinged with the first engaging member;
- a second engaging member rotatably coupled to the first arm;
- a second arm that extends in one direction and is hinged with the second engaging member; and
- a connection member having one end coupled to the diagnosis part and the other end hinged to the second arm.

7. The medical diagnosis apparatus of claim 1, wherein the first driving device is a traction motor, and the first sensor comprises an encoder configured to detect a driving state of the traction motor.

8. The medical diagnosis apparatus of claim 1, further comprising:
- an ultrasound diagnosis device comprising at least one ultrasound probe and a probe holder that is movably connected to the main body; and
- a second driving device configured to generate a driving force for moving the ultrasound diagnosis device,
wherein the ultrasound diagnosis device is spaced apart from the chair unit by a preset second distance in the one plane, and the controller is further configured to generate a control signal for moving the ultrasound diagnosis device according to the preset information.

9. The medical diagnosis apparatus of claim 8, wherein the chair unit and the ultrasound diagnosis device are spaced apart from each other by a preset second height along a direction perpendicular to the one plane.

10. The medical diagnosis apparatus of claim 9, further comprising:
- a second sensor configured to detect a position of the ultrasound diagnosis device, which varies depending on the driving force generated by the second driving device; and
- a second limit switch configured to stop the second driving device as the diagnosis part and the chair unit are arranged adjacent to each other with a distance or a height therebetween that is less than or equal to the preset second distance or the preset second height.

11. The medical diagnosis apparatus of claim 8, wherein the second distance that is a distance between a center line in the longitudinal direction of the chair unit and a center line of the probe holder extending in a direction parallel to the center line is in a range of 35 cm to 85 cm.

12. The medical diagnosis apparatus of claim 9, wherein the chair unit comprises an upper body support, a seat, and a leg rest sequentially arranged in one direction and connected to one another, and
wherein the second height between the seat and a lower end of the probe holder is in a range of 5 cm to 70 cm.

13. The medical diagnosis apparatus of claim 8, further comprising a probe sensor configured to detect a state in which the at least one ultrasound probe has been held on the probe holder.

* * * * *